US011771770B2

(12) United States Patent
Keidar et al.

(10) Patent No.: US 11,771,770 B2
(45) Date of Patent: Oct. 3, 2023

(54) COMPOSITIONS FOR TREATMENT OF CANCER, METHODS AND SYSTEMS FOR FORMING THE SAME

(71) Applicant: The George Washington University, Washington, DC (US)

(72) Inventors: Michael Keidar, Baltimore, MD (US); Zhitong Chen, Ashburn, VA (US); Xiaoqian Cheng, Falls Church, VA (US); Li Lin, Arlington, VA (US)

(73) Assignee: The George Washington University, Washington, DC (US)

( * ) Notice: Subject to any disclaimer, the term of this patent is extended or adjusted under 35 U.S.C. 154(b) by 1388 days.

(21) Appl. No.: 16/076,651

(22) PCT Filed: Mar. 16, 2017

(86) PCT No.: PCT/US2017/022766
§ 371 (c)(1),
(2) Date: Aug. 8, 2018

(87) PCT Pub. No.: WO2017/161153
PCT Pub. Date: Sep. 21, 2017

(65) Prior Publication Data
US 2019/0076537 A1 Mar. 14, 2019

Related U.S. Application Data

(60) Provisional application No. 62/310,178, filed on Mar. 18, 2016.

(51) Int. Cl.
*H05H 1/48* (2006.01)
*A61K 47/46* (2006.01)
(Continued)

(52) U.S. Cl.
CPC .............. *A61K 47/46* (2013.01); *A61B 18/02* (2013.01); *A61K 9/08* (2013.01); *A61K 47/26* (2013.01);
(Continued)

(58) Field of Classification Search
CPC .......... H05H 1/2406; H05H 1/46; H05H 1/24; H05H 1/48; H05H 2240/20; H05H 1/2418;
(Continued)

(56) References Cited

U.S. PATENT DOCUMENTS

2010/0209293 A1* 8/2010 Ikawa ...................... C02F 1/50
422/186
2012/0184014 A1 7/2012 Mascharak
(Continued)

FOREIGN PATENT DOCUMENTS

CN 102671850 A 9/2012
CN 105396227 A 3/2016
(Continued)

OTHER PUBLICATIONS

Hong, Translation of KR101256577B1, 2013 (Year: 2013).*
(Continued)

Primary Examiner — Renan Luque
(74) Attorney, Agent, or Firm — Blank Rome LLP

(57) ABSTRACT

Solutions having a solvent and a cold atmospheric plasma dissolved in the solvent are described. Methods and systems of forming cold atmospheric plasma (CAP)-containing solutions are also described. A system for producing (CAP)-containing solutions includes a gas source; a plasma generating device having a hollow body fluidically coupled with the gas source, a closed proximal end and an open distal end, the hollow body receiving gas from the gas source, and at least one electrode in or about the hollow body and ionizing (Continued)

the gas to discharge a cold atmospheric plasma (CAP) from the open distal end; and a container for housing a fluid, the open distal end of the plasma generating device in fluid communication with an inner portion of the container. CAP-containing solutions can be used in treatment of cancer cells, infected tissue sterilization, microorganism inactivation, promotion of wound healing, skin regeneration, and blood coagulation, and teeth bleaching/whitening.

11 Claims, 13 Drawing Sheets

(51) Int. Cl.
*A61L 15/46* (2006.01)
*A61L 15/42* (2006.01)
*A61L 15/44* (2006.01)
*H01J 37/32* (2006.01)
*A61P 35/00* (2006.01)
*A61B 18/02* (2006.01)
*A61K 9/08* (2006.01)
*A61K 47/26* (2006.01)
*A61B 18/00* (2006.01)

(52) U.S. Cl.
CPC .............. *A61L 15/42* (2013.01); *A61L 15/44* (2013.01); *A61L 15/46* (2013.01); *A61P 35/00* (2018.01); *H01J 37/32* (2013.01); *H05H 1/481* (2021.05); *A61B 2018/00583* (2013.01); *A61L 2300/404* (2013.01); *A61L 2300/416* (2013.01); *A61L 2300/60* (2013.01); *H05H 2242/10* (2013.01); *H05H 2245/20* (2021.05); *H05H 2277/10* (2013.01)

(58) Field of Classification Search
CPC ...... H05H 1/466; H05H 2240/10; H05H 1/30; H05H 2245/30; H05H 2242/20; H05H 2245/36; H05H 1/42; H05H 1/34; H05H 1/2431; H05H 1/2443; H05H 1/2465; H05H 2277/10
See application file for complete search history.

(56) References Cited

U.S. PATENT DOCUMENTS

| 2013/0062014 | A1* | 3/2013 | Koo | ...................... | B23K 10/00 |
| | | | | | 156/345.11 |
| 2015/0102255 | A1* | 4/2015 | Imai | ........................ | H05H 1/48 |
| | | | | | 422/186.04 |
| 2019/0284449 | A1* | 9/2019 | Koops | ...................... | C09J 7/401 |

FOREIGN PATENT DOCUMENTS

KR              101256577 B1 * 4/2013
WO     WO-2017055002 A1 * 4/2017

OTHER PUBLICATIONS

V. Boxhammer, et al., "Bactericidal Action of Cold Atmospheric Plasma in Solution", New Journal of Physics, http://www.njp.org; vol. 14, No. 11, Nov. 2012, pp. 3-8.
Z. Chen, et al., "Effects of Cold Atmospheric Plasma Generated in Deionized Water in Cell Cancer Therapy", Plasma Processes and Polymers, Dec. 2016, vol. 13, No. 12, 17 pgs.
J. L. Zimmermann, et al., "Effects of Cold Atmospheric Plasmas on Adenoviruses in Solution", Journal of Physics D: Applied Physics, vol. 44, No. 50, Nov. 2011, pp. 3-5, 7-8.
O. Volotskova, et al., "Integrin Activation by a Cold Atmospheric Plasma Jet", New Journal of Physics, vol. 14, No. 5, May 2012, pp. 16 pgs.
C. Weiz, et al., "Effects of Cold Atmospheric Plasma on Mucosal Tissue Culture", Journal of Physics D: Applied Physics, vol. 46, No. 4, Dec. 2012, 9 pgs.
International Search Report for PCT/US2017/022766 dated Jul. 19, 2017, 3 pages.

* cited by examiner

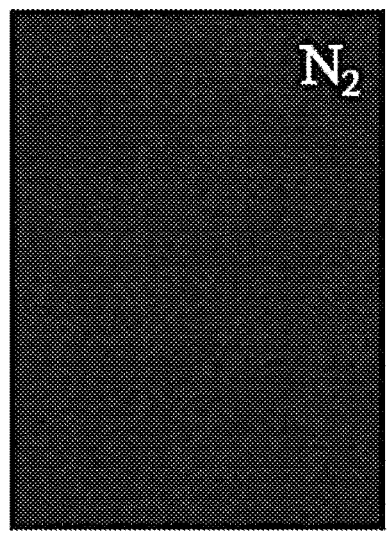
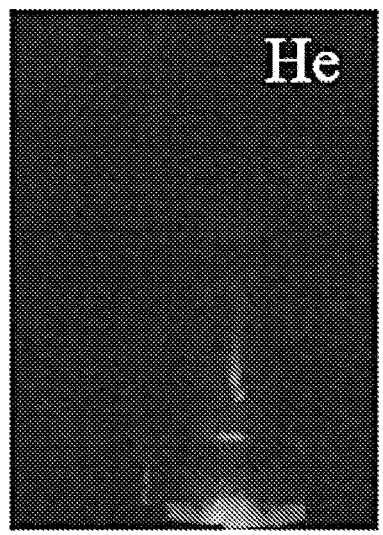
FIG. 8  FIG. 9  FIG. 10
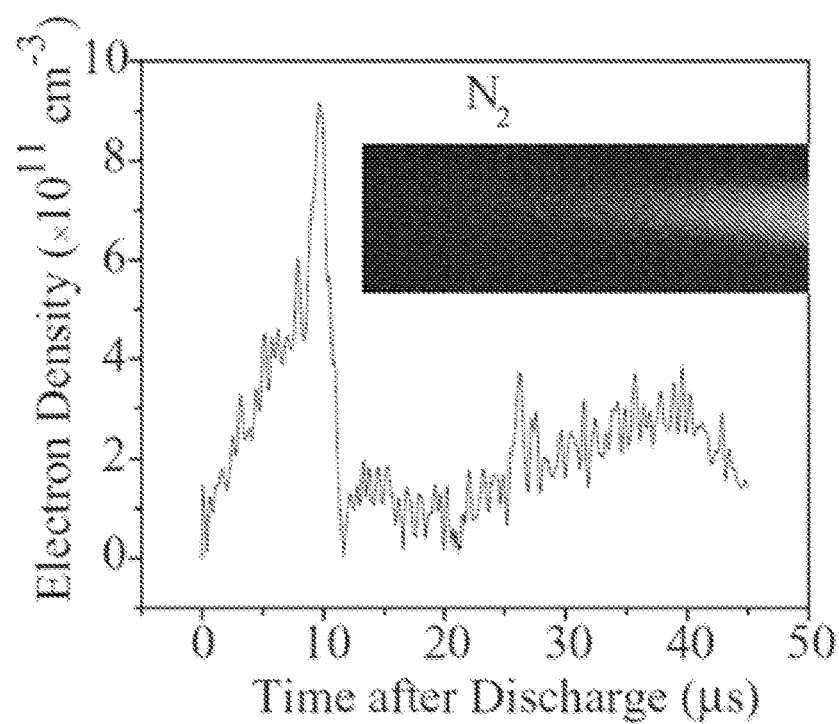
FIG. 11

COMPOSITIONS FOR TREATMENT OF CANCER, METHODS AND SYSTEMS FOR FORMING THE SAME

CROSS-REFERENCE TO RELATED APPLICATIONS

This application is a national stage of International Patent Application No. PCT/US2017/022766, filed Mar. 16, 2017, which claims the benefit of U.S. provisional application No. 62/310,178, filed Mar. 18, 2016, the contents of which are incorporated by reference herein in their entirety.

GOVERNMENT LICENSE RIGHTS

This invention was made with Government support under Grant No. 1465061 awarded by the National Science Foundation. The U.S. Government has certain rights in this invention.

FIELD OF TECHNOLOGY

The present application relates to cold atmospheric plasma (CAP)-containing solutions. The present application further relates to systems and methods for the production of CAP-containing solutions. The present application yet further relates to the use of CAP-containing solutions for the sterilization of infected tissues, inactivation of microorganisms, promotion of wound healing, promotion of skin regeneration, promotion of blood coagulation, the bleaching/whitening of teeth, and the treatment of cancer cells.

BACKGROUND

For successful cancer therapy, the most important aspect is selective eradication of cancer cells with minimal harm to surrounding healthy tissue. Cancer cells as well as normal cells generally generate reactive oxygen species (ROS) and reactive nitrogen species (RNS). ROS and RNS are able to induce cell proliferation as well as cell death, while extreme amounts of reactive species (RS) can induce apoptosis and damage proteins, lipids, and deoxyribonucleic acid (DNA).

Plasma is a fully or partially ionized gas consisting of positive and negative ions, free electrons, free radicals, ozone, and ultraviolet radiation. Historically, plasma could be generated only at high temperatures or in vacuum, while more recent studies have reported on plasma generated at atmospheric pressure and at room temperature. Plasma generated at atmospheric pressure and at room temperature is commonly known as cold atmospheric plasma (CAP, sometimes referred to as non-thermal atmospheric plasma (NTAP)). Recently, CAP has been introduced as a tool with a potential to shift the current paradigm of cancer treatment. In general, CAP has shown potential for use in various biomedical applications such as sterilization of infected tissues, inactivation of microorganisms, wound healing, skin regeneration, blood coagulation, and tooth bleaching. CAP is known for the generation of various RS that affect various cellular functions. CAP produces a level of reaction chemistry and unique chemical composition similar to endogenous ROS/RNS cell chemistry. CAP produces variety of ultraviolet (UV), charged particles (electrons, ions), electronically excited atoms, ROS such as the hydroxyl radical (·OH), RNS such as nitric oxide radical (·NO), and superoxide radicals.

CAP has had significant success in both in vitro and in vivo studies for the irradiation of various forms of cancer. In such studies, however, CAP is directly jetted onto the cancerous and surrounding tissues, which limits application of CAP to only the skin of a patient or, if the cancerous tissue is located inside the patient, requires invasive surgical procedures followed by injection of CAP into one or more internal cavities of a patient. Furthermore, direct CAP jetting only results in the cell death in the upper 3-5 cell layers of the tissues in contact with the CAP, whether used externally or internally on a patient.

BRIEF SUMMARY OF THE DRAWINGS

The accompanying figures illustrate embodiments and serve to explain principles of the disclosed embodiments. It is to be understood, however, that these figures are presented for purposes of illustration only, and not for defining limits of the present invention.

FIG. 8 is an image of plasma generated in DI water from $N_2$ gas using a system according FIG. 1, in accordance with various embodiments of the present disclosure;

FIG. 9 is an image of plasma generated in DI water from He gas using a system according FIG. 1, in accordance with various embodiments of the present disclosure;

FIG. 10 is an image of plasma generated in DI water from Ar gas using a system according FIG. 1, in accordance with various embodiments of the present disclosure;

FIG. 11 is a graphical representation of the electron density of plasma generated in DI water from $N_2$ gas, and an intensified charged-coupled device (ICCD) image (inset) of the corresponding plasma generated in the DI water, using a system in accordance with FIG. 2, in accordance with various embodiments of the present disclosure;

DETAILED DESCRIPTION

Figure 1:
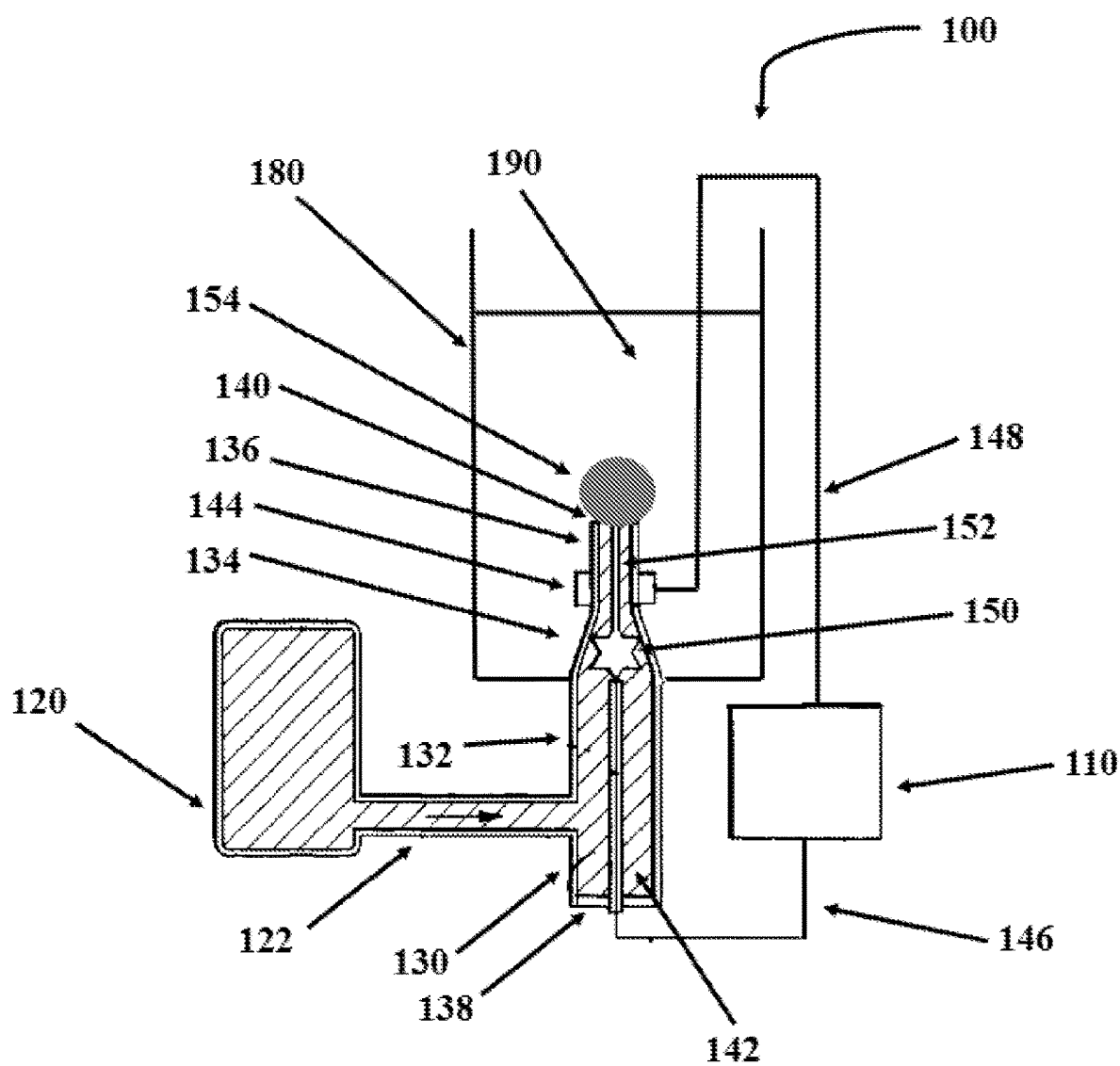
FIG. 1 is an illustration of a system for the formation of a cold atmospheric plasma (CAP)-containing solution, in accordance with various embodiments of the present disclosure.

Exemplary, non-limiting embodiments of the present application will now be described with references to the above-mentioned figures. Particularly, embodiments of the application comprise parts or method steps that are similar or identical to each other. These parts or method steps are thus denoted with similar or identical names or reference numerals. Description of these relevant parts of method steps is hereby incorporated by reference, wherever relevant or appropriate.

As used throughout, ranges are used as shorthand for describing each and every value that is within the range. Any value within the range can be selected as the terminus of the range.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent, alternatively ±5 percent, and alternatively ±1 percent of the given numeric value provided such a deviation does not alter the end function or result of the value. Accordingly, unless indicated to the contrary, the numerical parameters set forth in this specification and attached claims are approximations that can vary depending upon the desired properties sought to be obtained by the present invention.

The term "plasma" refers to a fully or partially ionized gas which may include one or more of positive and negative ions, free electrons, free radicals, ozone, and ultraviolet radiation. The term "cold atmospheric plasma" refers to a plasma generated at atmospheric pressure and at room temperature. The term "fluid" as used herein can mean a liquid, a gas, or a plasma, or any combination thereof.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises"), "include" (as well as forms, derivatives, or variations thereof, such as "including" and "includes") and "has" (as well as forms, derivatives, or variations thereof, such as "having" and "have") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

For the purposes of this specification and appended claims, the term "coupled" refers to the linking or connection of two objects. The coupling can be permanent or reversible. The coupling can be direct or indirect. An indirect coupling includes connecting two objects through one or more intermediary objects. The term "fluidically coupled" refers to the permanent or reversible, direct or indirect, linking or connection of two objects such that fluids may flow, in a single direction or in more than one direction, from one object to another. The term "fluid communication" refers to objects which are in contact with, but not necessarily coupled with or connected to, one another, whereby a fluid can pass from one object to the other. The term "substantially" refers to an element essentially conforming to the particular dimension, shape or other word that substantially modifies, such that the component need not be exact. For example, substantially cylindrical means that the object resembles a cylinder, but can have one or more deviations from a true cylinder.

FIG. 1 is an illustration of a system for the formation of a CAP-containing solution in accordance with various embodiments of the present disclosure. The system 100 includes a power supply 110, a gas source 120, a plasma formation chamber 130, and a container 180 configured to hold a fluid 190 therein. The gas source 120 is fluidically coupled with the plasma formation chamber 130 via a tube 122. In some instances, the fluid 190 is deionized (DI) water. In other instances, the fluid 190 can be any one of a water-based electrolyte solution, a phosphate-buffered saline (PBS) solution, a glucose solution, a cell culture medium, or any suitable combination thereof. The culture medium can be, but is not limited to, Dulbecco's Modified Eagle Medium (DMEM, from Life Technologies) or Roswell Park Memorial Institute (RPMI)-1640 Medium (ATCC® 30-2001™), or a culture medium having amino acids (for example, phenylalanine, alanine, histidine, arginine, tyrosine, tryptophan, lysine or derivatives thereof) incorporated therein at a concentration ranging from about 5 millimolar (mM) to about 30 mM. In yet other instances, the fluid 190 can be a biocompatible hydrogel, a solution comprising a biocompatible solvent and a biocompatible polymer, or gelatin.

The plasma formation chamber 130 can be made of a glass, a rigid or flexible plastic, or any other suitable material known to one of ordinary skill in the art. The plasma formation chamber 130 includes a main body 132, an inwardly tapering portion 134, and a neck 136. The main body 132 has a proximal gas-tight seal 138 and the neck 136 has a distal opening or nozzle 140 for the discharge of a plasma therefrom into the fluid 190. A central powered electrode 142 extends longitudinally through the proximal gas-tight seal 138 and the main body 132, terminating near the inwardly tapered portion 134. The central powered electrode 142 is surrounded by insulation except at its distal end which faces the inwardly tapering portion 134.

An annular grounded electrode 144 is located around an outer surface of the neck 136 of the plasma formation chamber 130. The power supply 110 is electrically coupled with the central powered electrode 142 and the annular grounded electrode 144 via insulated wires 146 and 148, respectively, to provide a high voltage supply thereto. As illustrated in FIG. 1, at least a portion of the distal opening 140, inwardly tapering portion 134, the neck 136 and the annular grounded electrode 144 are submerged in the fluid 190 at the interior of the container 180, while at least a portion of the main body 132 remains at the exterior of the container 180. In some instances, only the neck 136 and the annular grounded electrode 144 are submerged in the fluid 190, and the tapered portion 134 and main body 132 remain at the exterior of the container 180. In other instances, a portion of the inwardly tapering portion 134, the neck 136 and the annular grounded electrode 144 are submerged in the fluid 190, and a portion of the tapered portion 134 and main body 132 are at the exterior of the container 180. In yet other instances, a portion of the main body 132, the inwardly tapering portion 134, the neck 136 and the annular grounded electrode 144 are submerged in the fluid 190, and a portion of the main body 132 is at the exterior of the container 180. One of ordinary skill in the art can vary the degree in which one or more of the main body 132, the tapered portion 134, and the neck 136 are submerged into the fluid 190 to maximize the efficiency of CAP-containing solution formation. In any of the above instances, the plasma formation chamber 130 and the container 180 are coupled to each other to form a seal such that the fluid 190 does not leak therebetween.

In use, a gas is transmitted from the gas source 120 to the main body 132 of the plasma formation chamber 130 via the tube 122. The gas source 120 can be pressurized. In some instances, the gas is compressed argon. In other instances, the gas is compressed nitrogen. In other instances, the gas is compressed helium. In yet other instances, the gas can be compressed air. The gas can be reaction grade (i.e., pure), substantially pure (i.e., contain minor amounts of impurities), or industrial grade. In general, the gas can be can any gas suitable for formation of a plasma that can readily dissolve or diffuse into the fluid 190. In some instances, the gas source 120 can be fluidically coupled with the tube 122 via gas flow regulator (not shown) to control the amount of gas delivered to the main body 132 of the plasma formation chamber 130 per unit time. The gas flow regulator can further include a one-way check valve.

The gas travels through the main body 132 of the plasma formation chamber 130, is ionized by the distal end of the central powered electrode 142 and the annular grounded electrode 144 to form a cold atmospheric plasma 150 (illustrated herein in the shape of a star, but the plasma 150 does not necessarily form in such a shape) at a discharge area in the inwardly tapering portion 134 of the plasma formation chamber 130. The decrease in diameter at the inwardly tapering portion 134 causes an increase of gas density therein which promotes ionization of the gas and, by extension, plasma formation. The plasma 150 then travels through and exits the neck 136 of the plasma formation chamber 130 as a jet or stream flow 152. The jet or stream flow 152 can form a plasma bubble 154 in the fluid 190. As one of ordinary skill in the art may appreciate, the circular shape of the plasma bubble 154 in FIG. 1 is for illustrative purposes only. Furthermore, the plasma bubble 154 may not be a single plasma bubble but, instead, may be multiple plasma bubbles. Without being bound to any particular theory, the shape and size of the plasma bubble 154 may depend upon the flow rate of the gas from the gas source 120, the rate of formation of the plasma 150, the exit velocity of the plasma 150 from the plasma formation chamber 130 into the fluid 190, the temperature and viscosity of the fluid 190, and other experimental parameters. Furthermore, as can be appreciated by one of ordinary skill in the art, as the rate of gas supplied to the plasma formation chamber 130 is increased, the probability of plasma bubble 154 formation decreases while the probability of the formation of the plasma jet or stream 152 increases. FIGS. 8-10 provide visual examples of the jet or stream flow 152 formed in accordance with the system 100 of FIG. 1. The plasma bubble 154 can subsequently dissolve or diffuse in the fluid 190 to form the final product, a cold atmospheric plasma (CAP)-containing solution.

Formation of the CAP-containing solution can be accomplished by continuous or incremental plasma generation over a period of time ranging from about 30 seconds to about 1 hour. Alternatively, formation of the CAP-containing solution can be accomplished by continuous or incremental plasma generation over a period of time ranging from about 1 minute to about 45 minutes. Alternatively, formation of the CAP-containing solution can be accomplished by continuous or incremental plasma generation over a period of time ranging from about 5 minutes to about 30 minutes.

In some instances, the gas can be supplied from the gas source 120 to the plasma formation chamber 130 at a rate ranging from about 0.5 liters (L)/minute (min) to about 20 L/min. Alternatively, the gas can be supplied from the gas source 120 to the plasma formation chamber 130 at a rate ranging from about 1 L/min to about 10 L/min. Alternatively, the gas can be supplied from the gas source 120 to the plasma formation chamber 130 at a rate ranging from about 2 L/min to about 5 L/min. Alternatively, the gas can be supplied from the gas source 120 to the plasma formation chamber 130 at a rate ranging from about 3 L/min to about 4 L/min.

In some instances, the voltage applied to the plasma formation chamber 130 by the central powered electrode 142 and the annular grounded electrode 144 can range from about 1 kilovolt (kV) to about 15 kV. Alternatively, the voltage applied can range from about 2 kV to about 8 kV. Alternatively, the voltage can range from about 2 kV to about 5 kV. In some instances, the applied voltage can have a frequency ranging from about 5 kilohertz (kHz) to about 45 kHz. Alternatively, the applied voltage can have a frequency ranging from about 15 kHz to about 40 kHz. Alternatively, the applied voltage can have a frequency ranging from about 20 kHz to about 35 kHz. Alternatively, the applied voltage can have a frequency ranging from about 25 kHz to about 35 kHz. Alternatively, the applied voltage can have a frequency ranging from about 30 kHz to about 35 kHz. Of course, other suitable values can be provided for the rates and voltages, within the scope of the present disclosure.

In system 100, at least a portion of the distal opening 140, inwardly tapering portion 134, the neck 136 and the annular grounded electrode 144 are submerged in the fluid 190 at the interior of the container 180, through a bottom surface of the container 180. However, it will be recognized that the distal opening 140, tapering portion 134, neck 136, and/or electrode 144 can enter the container 180 in any suitable manner, such as through a sidewall of the container 180. When at least a portion of the distal opening 140, inwardly tapering portion 134, the neck 136 and the annular grounded electrode 144 are submerged in the fluid 190 at the interior of the container 180, through a sidewall of the container 180, the plasma formation chamber 130 and the sidewall of the container 180 are coupled to each other to form a seal such that the fluid 190 does not leak therebetween.

Figure 2:
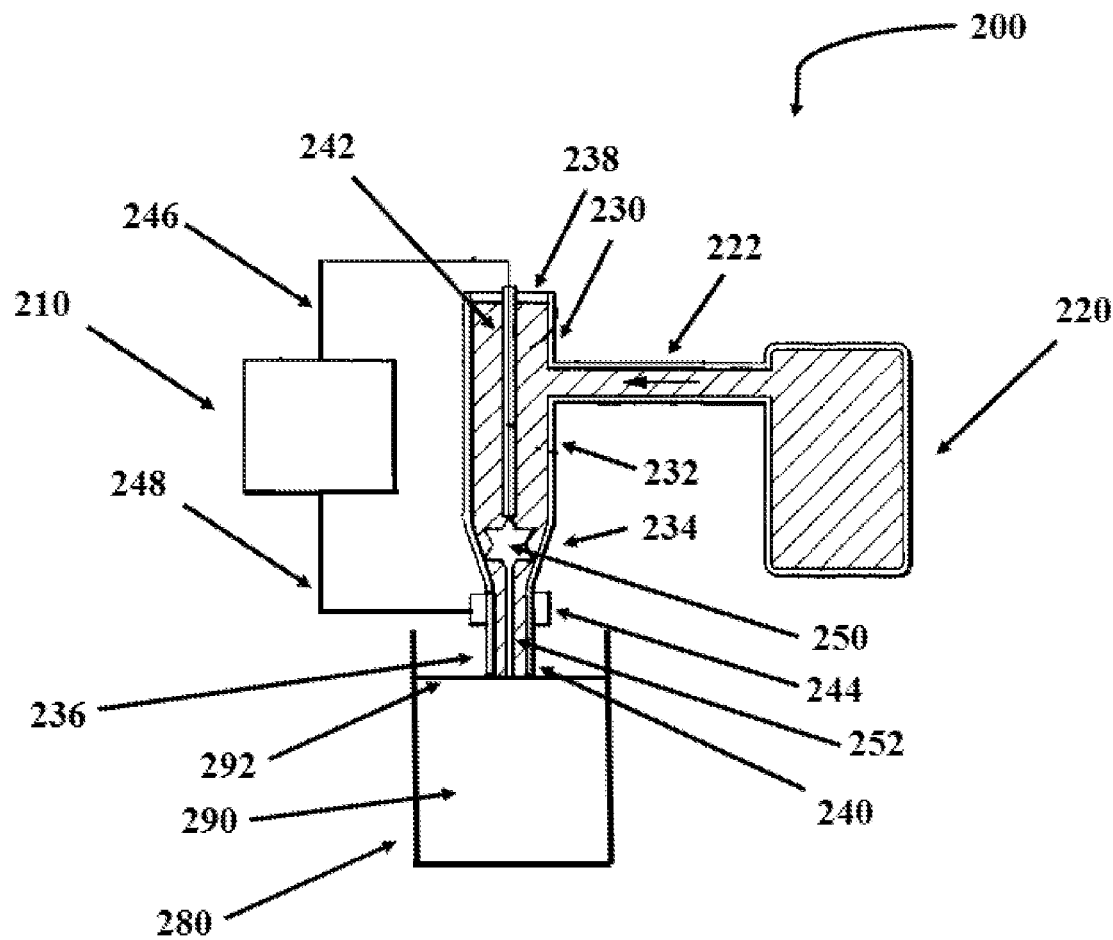
FIG. 2 is an illustration of another system for the formation of a CAP-containing solution, in accordance with various embodiments of the present disclosure.

FIG. 2 is an illustration of another system for the formation of a CAP-containing solution in accordance with various embodiments of the present disclosure. The system 200 includes a power supply 210, a gas source 220, a plasma formation chamber 230, and a container 280 configured to hold a fluid 290 therein. The gas source 220 is fluidically coupled with the plasma formation chamber 230 via a tube 222. In some instances, the fluid 290 is deionized (DI) water. In other instances, the fluid 290 can be any one of a water-based electrolyte solution, a phosphate-buffered saline (PBS) solution, a glucose solution, a cell culture medium, or any suitable combination thereof. The culture medium can be, but is not limited to, DMEM or RPMI-1640, a culture medium having amino acids (for example, phenylalanine, alanine, histidine, arginine, tyrosine, tryptophan, lysine or derivatives thereof) incorporated therein at a concentration ranging from about 5 millimolar (mM) to about 30 mM. In yet other instances, the fluid 290 can be a biocompatible hydrogel, a solution comprising a biocompatible solvent such as DI water and a biocompatible polymer, or gelatin.

The plasma formation chamber 230 can be made of a glass, a rigid or flexible plastic, or any other suitable material known to one of ordinary skill in the art. The plasma formation chamber 230 includes a main body 232, an inwardly tapering portion 234, and a neck 236. The main body 232 has a proximal gas-tight seal 238 and the neck 236 has a distal opening or nozzle 240 for the discharge of a plasma therefrom into the fluid 290.

A central powered electrode 242 extends longitudinally through the proximal gas-tight seal 238 and the main body 232, terminating near the inwardly tapered portion 234. The central powered electrode 242 is surrounded by insulation except at its distal end which faces the inwardly tapering portion 234. An annular grounded electrode 244 is located around an outer surface of the neck 236 of the plasma formation chamber 230. The power supply 210 is electrically coupled with the central powered electrode 142 and the annular grounded electrode 244 via insulated wires 246 and 248, respectively, to provide a high voltage supply thereto.

The fluid 290 is defined by a fluid line 292. In some instances, the distal opening or nozzle 240 is positioned above and in close proximity to the fluid line 292 (for example, 0.5-3 centimeters). In some instances, the distal opening or nozzle 240 is positioned to touch the fluid line 292 such that distal opening or nozzle 240 terminates in the same plane as the fluid line 292. In some instances, the distal opening or nozzle 240 is positioned below the fluid line 292 such that at least a portion of the neck 236 is submerged in the fluid 290. In some instances, the distal opening or nozzle 240 is positioned below the fluid line 292 such that the neck 236 and the annular grounded electrode 244 is submerged in the fluid 290. In some instances, the distal opening or nozzle 240 is positioned below the fluid line 292 such that the neck 236, the annular grounded electrode 244, and at least a portion of the inwardly tapering portion 234 is submerged in the fluid 290. In some instances, the distal opening or nozzle 240 is positioned below the fluid line 292 such that the neck 236, the annular grounded electrode 244, the inwardly tapering portion 234, and at least a portion of the main body 232 is submerged in the fluid 290.

Figure 12:
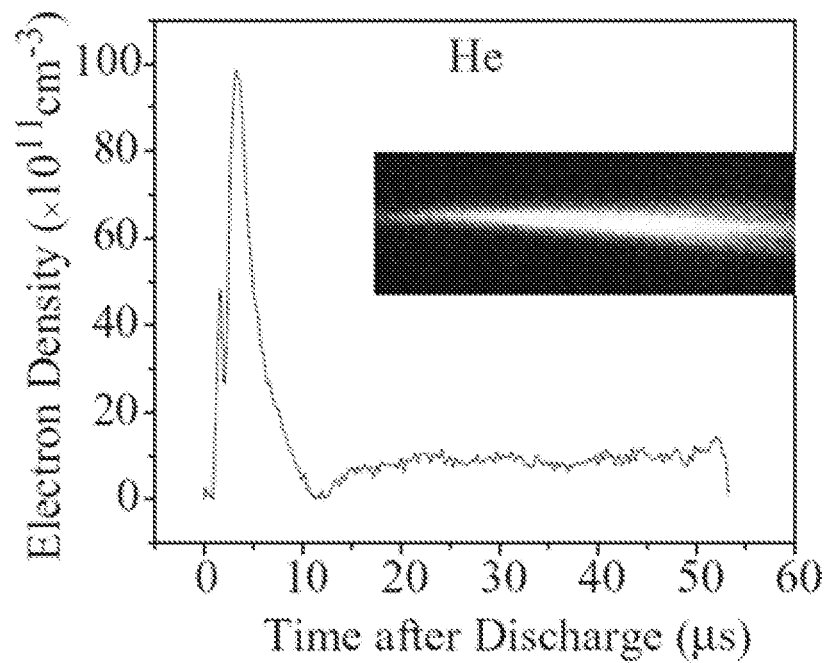
FIG. 12 is a graphical representation of the electron density of plasma generated in DI water from He gas, and an ICCD image (inset) of the corresponding plasma generated in the DI water, using a system in accordance with FIG. 2, in accordance with various embodiments of the present disclosure.
Figure 13:
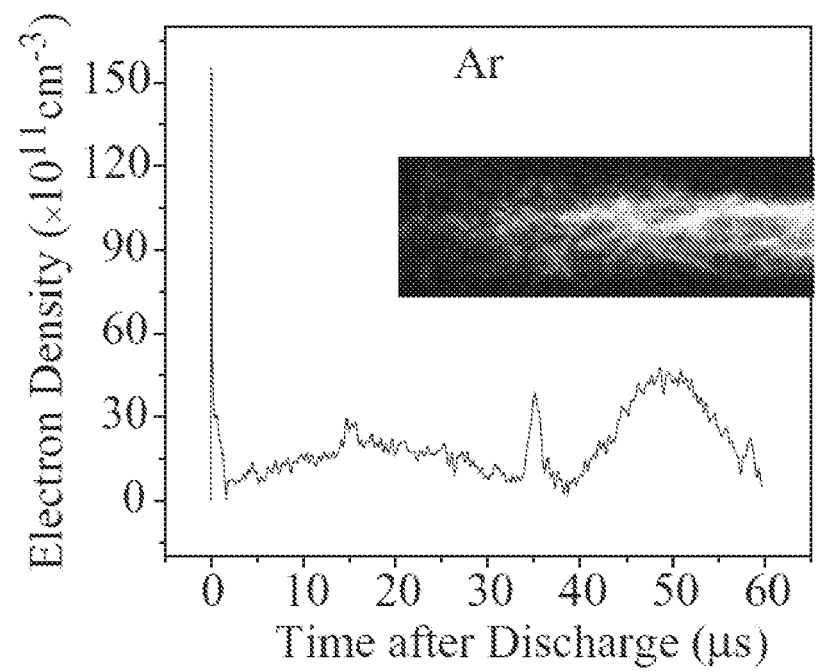
FIG. 13 is a graphical representation of the electron density of plasma generated in DI water from Ar gas, and an ICCD image (inset) of the corresponding plasma generated in the DI water, using a system in accordance with FIG. 2, in accordance with various embodiments of the present disclosure.

In use, a gas is transmitted from the gas source 220 to the main body 232 of the plasma formation chamber 230 via the tube 222. The gas source 220 can be pressurized. In some instances, the gas is compressed argon. In other instances, the gas is compressed nitrogen. In other instances, the gas is compressed helium. In yet other instances, the gas can be compressed air. The gas can be reaction grade (i.e., pure), substantially pure (i.e., contain minor amounts of impurities), or industrial grade. In general, the gas can be any gas suitable for formation of a plasma that can readily dissolve or diffuse into the fluid 290. In some instances, the gas source 220 can be fluidically coupled with the tube 222 via gas flow regulator (not shown) to control the amount of gas delivered to the main body 232 of the plasma formation chamber 230 per unit time. The gas flow regulator can include a one-way check valve. The gas travels through the main body 232 of the plasma formation chamber 230, is ionized by the distal end of the central powered electrode 242 and the annular grounded electrode 244 to form a cold atmospheric plasma 250 (illustrated herein in the shape of a star, but the plasma 150 does not necessarily form in such a shape) at a discharge area in the inwardly tapering portion 234 of the plasma formation chamber 230. The plasma 250 then travels through and exits the neck 236 of the plasma formation chamber 230 as a jet or stream flow 252 into the fluid 290. The jet or stream flow 252 can dissolve or diffuse in the fluid 290 at a liquid interface, or the fluid line 292, of the fluid 290 to form the final product, a cold atmospheric plasma (CAP)-containing solution. FIGS. 11-13 provide visual examples of the jet or stream flow 252 formed in accordance with the system 200 of FIG. 2.

Accordingly, the embodiment of FIG. 2 does not utilize a plasma bubble, as in FIG. 1. Instead, the formed plasma 250 can be applied to the fluid 290 externally, so that no bubble is formed. Rather, the jet or stream flow 252 of the plasma 250 interacts with the liquid interface, or the fluid line 292, and the CAP-containing solution is formed at the liquid interface.

Formation of the CAP-containing solution can be accomplished by continuous or incremental plasma generation over a period of time ranging from about 30 seconds to about 1 hour. Alternatively, formation of the CAP-containing solution can be accomplished by continuous or incremental plasma generation over a period of time ranging from about 1 minute to about 45 minutes. Alternatively, formation of the CAP-containing solution can be accomplished by continuous or incremental plasma generation over a period of time ranging from about 5 minutes to about 30 minutes.

In some instances, the gas can be supplied from the gas source 220 to the plasma formation chamber 230 at a rate ranging from about 0.5 L/min to about 20 L/min. Alternatively, the gas can be supplied from the gas source 220 to the plasma formation chamber 230 at a rate ranging from about 1 L/min to about 10 L/min. Alternatively, the gas can be supplied from the gas source 220 to the plasma formation chamber 230 at a rate ranging from about 2 L/min to about 5 L/min. Alternatively, the gas can be supplied from the gas source 220 to the plasma formation chamber 230 at a rate ranging from about 3 L/min to about 4 L/min.

In some instances, the voltage applied to the plasma formation chamber 230 by the central powered electrode 242 and the annular grounded electrode 144 can range from about 1 kV to about 15 kV. Alternatively, the voltage applied can range from about 2 kV to about 8 kV. Alternatively, the voltage can range from about 2 kV to about 5 kV. In some instances, the applied voltage can have a frequency ranging from about 5 kHz to about 45 kHz. Alternatively, the applied voltage can have a frequency ranging from about 15 kHz to about 40 kHz. Alternatively, the applied voltage can have a frequency ranging from about 20 kHz to about 35 kHz. Alternatively, the applied voltage can have a frequency ranging from about 25 kHz to about 35 kHz. Alternatively, the applied voltage can have a frequency ranging from about 30 kHz to about 35 kHz.

Systems 100 and 200, while having plasma formation chambers with different orientations and locations relative to the fluid in which a CAP-containing solution is formed, have both been found to efficiently produce said CAP-containing solutions. System 100 may be preferred, in some instances, due to the rate of formation of a plasma bubble at certain gas supply rates and higher overall yield of CAP-containing solutions. In other instances, system 200 may be preferred due to easier assembly and longer-term stability of the system 200.

CAP-containing solutions formed using either system 100 or system 200 can contain reactive oxygen species (ROS) such as, but not limited to, hydroxyl radicals (·OH), hydrogen peroxide ($H_2O_2$), singlet oxygen ($^1O_2$), and superoxide radicals ($·O_2^-$). CAP-containing solutions formed using either system 100 or system 200 can also contain reactive nitrogen species (RNS) such as, but not limited to nitric oxide (·NO), nitrogen cation ($N_2^-$), nitrite ion ($NO_2^-$), and peroxynitrite ion ($ONOO^-$). In some instances, the CAP-containing solutions can have $H_2O_2$ concentrations (micromolar; μM) ranging from about 0.5 μM to about 25 μM. In some instances, the CAP-containing solutions can have $NO_2^-$ concentrations ranging from about 0.5 μM to about 25 μM.

After formation of a CAP-containing solution, the solution can be stored at a temperature ranging from about 25° C. to about −40° C., alternatively about 10° C. to about −30° C., alternatively about 8° C. to about −30° C., and alternatively about 2° C. to about −25° C. Preferably, CAP-containing solutions formed according to the present disclosure are also stored in a dark location. Storage under such conditions may result in a shelf life of the CAP-containing solution on the order of days to months.

In some instances, CAP-containing solutions formed according to various embodiments of the present disclosure can be used for the sterilization of infected tissues. In other instances, CAP-containing solutions formed according to various embodiments of the present disclosure can be used for the inactivation of microorganisms. In yet other instances, CAP-containing solutions formed according to various embodiments of the present disclosure can be used to promote wound healing. In yet other instances, CAP-containing solutions formed according to various embodiments of the present disclosure can be used to promote skin regeneration. In yet other instances, CAP-containing solutions formed according to various embodiments of the present disclosure can be used to promote blood coagulation. In yet other instances, CAP-containing solutions formed according to various embodiments of the present disclosure can be used to for the bleaching or whitening of teeth. In yet other instances, CAP-containing solutions formed according to various embodiments of the present disclosure can be to kill cancer cells. The cancer cells can be, but are not limited to, breast cancer, lung carcinoma, hepatocellular carcinoma, neuroblastoma, skin carcinoma, melanoma, colon carcinoma, pancreatic carcinoma, bladder carcinoma, cervical carcinoma, gastric cancer, lymphoma, myeloma, soft tissue sarcoma, osteosarcoma, endometrial cancer, renal cell cancer, and mouth/oral cancer. CAP-containing solutions used in any of the above instances can contain reactive oxygen species (ROS) such as, but not limited to, hydroxyl radicals ($\cdot OH$), hydrogen peroxide ($H_2O_2$), singlet oxygen ($^1O_2$), and superoxide radicals ($\cdot O_2^-$), and can also contain reactive nitrogen species (RNS) such as, but not limited to nitric oxide ($\cdot NO$), nitrogen cation ($N_2^+$), nitrite ion ($NO_2^-$), and peroxynitrite ion ($ONOO^-$). Furthermore, the CAP-containing solutions used in any of the above instances can have $H_2O_2$ concentrations (micromolar; μM) ranging from about 0.5 μM to about 25 μM. In some instances, the CAP-containing solutions can have $NO_2^-$ concentrations ranging from about 0.5 μM to about 25 μM. The pharmaceutically acceptable amount of CAP-containing solution, and concentrations of ROS and RNS, used in the above instances can be tailored to the specific ailment, the degree, duration and intervals of required treatment, and to the specific limitations of the patient (i.e., body mass, overall state of immune system, etc.), as can be appreciated by one of ordinary skill in the art.

In instances where the application or use of a CAP-containing solution does not require invasive procedures, such as application on an external portion of a patient (for example, tooth whitening, skin regeneration, treatment of external cancer cells), the CAP-containing solution can be applied directly to the external tissue. In some instances, the CAP-containing solution can be absorbed into an absorbent material of a medical dressing such as for example, gauze, a pad, a wrap, a sponge or sponge-like material, or a compress. The medical dressing can then be applied to the external tissue of a patient for a predetermined period of treatment time. In some instances, CAP-containing solution can be applied to external tissue or easily accessible body cavities (such as for example, oral or sinus cavities) as a mist or spray. CAP-containing solutions used in any of the above instances can contain reactive oxygen species (ROS) such as, but not limited to, hydroxyl radicals ($\cdot OH$), hydrogen peroxide ($H_2O_2$), singlet oxygen ($^1O_2$), and superoxide radicals ($\cdot O_2^-$), and can also contain reactive nitrogen species (RNS) such as, but not limited to nitric oxide ($\cdot NO$), nitrogen cation ($N_2^+$), nitrite ion ($NO_2^-$), and peroxynitrite ion ($ONOO^-$). Furthermore, the CAP-containing solutions used in any of the above instances can have $H_2O_2$ concentrations (micromolar; μM) ranging from about 0.5 μM to about 25 μM. In some instances, the CAP-containing solutions can have $NO_2^-$ concentrations ranging from about 0.5 μM to about 25 μM. The pharmaceutically acceptable amount of CAP-containing solution, and concentrations of ROS and RNS, used in the above instances can be tailored to the specific ailment, the degree, duration and intervals of required treatment, and to the specific limitations of the patient (i.e., body mass, overall state of immune system, etc.), as can be appreciated by one of ordinary skill in the art.

In instances where the application or use of a CAP-containing solution may require invasive procedures such as for example, the treatment of cancer cells located on an internal organ, tissue or a cavity of a patient, a CAP-containing solution can be delivered to the internal organ, tissue or cavity using a needle or syringe, a needle-free injector, a catheter, a cannula, stent a G-Tube or feeding tube or any other suitable means of internal fluid delivery known to one of ordinary skill in the art. CAP-containing solutions used in any of the above instances can contain reactive oxygen species (ROS) such as, but not limited to, hydroxyl radicals ($\cdot OH$), hydrogen peroxide ($H_2O_2$), singlet oxygen ($^1O_2$), and superoxide radicals ($\cdot O_2^-$), and can also contain reactive nitrogen species (RNS) such as, but not limited to nitric oxide ($\cdot NO$), nitrogen cation ($N_2^+$), nitrite ion ($NO_2^-$), and peroxynitrite ion ($ONOO^-$). Furthermore, the CAP-containing solutions used in any of the above instances can have $H_2O_2$ concentrations (micromolar; μM) ranging from about 0.5 μM to about 25 μM. In some instances, the CAP-containing solutions can have $NO_2^-$ concentrations ranging from about 0.5 μM to about 25 μM. The pharmaceutically acceptable amount of CAP-containing solution, and concentrations of ROS and RNS, used in the above instances can be tailored to the specific ailment, the degree, duration and intervals of required treatment, and to the specific limitations of the patient (i.e., body mass, overall state of immune system, etc.), as can be appreciated by one of ordinary skill in the art.

In some instances, where the cancer is located in, for example, the stomach or esophagus, a CAP-containing solution can be administered orally to a patient by having the patient ingest a predetermined amount of the CAP-containing solution. In some instances where treatment of a cancer located on an internal organ, tissue or a cavity of a patient, a CAP-containing solution can be administered in the form of a pill or suppository. In such instances, the CAP-containing solution can be contained within a shell or coating. The shell or coating can be made to dissolve in time-elapsed manner for dime-elapsed release of the CAP-containing solution therefrom. CAP-containing solutions used in any of the above instances can contain reactive oxygen species (ROS) such as, but not limited to, hydroxyl radicals ($\cdot OH$), hydrogen peroxide ($H_2O_2$), singlet oxygen ($^1O_2$), and superoxide radicals ($\cdot O_2^-$), and can also contain reactive nitrogen species (RNS) such as, but not limited to nitric oxide ($\cdot NO$), nitrogen cation ($N_2^+$), nitrite ion ($NO_2^-$), and peroxynitrite ion ($ONOO^-$). Furthermore, the CAP-containing solutions used in any of the above instances can have $H_2O_2$ concentrations (micromolar; μM) ranging from about 0.5 μM to about 25 μM. In some instances, the CAP-containing solutions can have $NO_2^-$ concentrations ranging from about 0.5

μM to about 25 μM. The pharmaceutically acceptable amount of CAP-containing solution, and concentrations of ROS and RNS, used in the above instances can be tailored to the specific ailment, the degree, duration and intervals of required treatment, and to the specific limitations of the patient (i.e., body mass, overall state of immune system, etc.), as can be appreciated by one of ordinary skill in the art.

EXAMPLES

The following examples are intended to be illustrative only, and are not intended to be, nor should they be construed as, limiting in any way of the scope of the present disclosure.

Materials and Methods

Cancer cell lines. For the Examples below, the human breast adenocarcinoma cell line MDA-MB-231 (from American Type Culture Collection, ATCC®, or Sigma-Aldrich®) or the human gastric cancer line NCI-N87 (from ATCC®) were used. MDA-MD-231 cells were cultured in Dulbecco's Modified Eagle Medium (DMEM, from Life Technologies) supplemented with 10% v/v fetal bovine serum (from Atlantic Biologicals) and 1% v/v penicillin and streptomycin (from Life Technologies). NCI-N87 cells were cultured in RPMI-1640 Medium (ATCC® 30-2001™) supplemented with 10% v/v fetal bovine serum (from Atlantic Biologicals). Both cell cultures were maintained at 37° C. in a humidified incubator containing 5% v/v $CO_2$.

Production of CAP-containing solutions. To generate CAP-containing solutions, a system according FIG. 1, as described above, was utilized. The system included a central powered electrode (1 mm in diameter) and a grounded outer electrode wrapped around the outside of a quartz tube (4.5 mm in diameter). The electrodes were connected to a secondary high voltage power supply (voltage in the range of 2-5 kV, frequency of about 30 kHz). Industrial grade nitrogen ($N_2$), argon (Ar), and helium (He) were used as carrier gases. The flow rate was maintained at about 0.3 L/min. CAP treatment outside of DI water, using a system according to FIG. 2, was also used for comparison.

The above represent general parameters for the production of CAP-containing solutions. As will be discussed below, however, one or more of the above parameters may have been modified in some examples.

Optical emission Spectroscopy (OES) and ultra-violet-visible-near infrared (UV-vis-NIR. OES and UV-visible-NIR were used to qualitatively detect various RNS and ROS (i.e., nitrogen ($N_2$), nitric oxide radical (·NO), nitrogen cation ($N_2^+$), atomic oxygen (O), and hydroxyl radical (·OH)) from plasma discharged in water at wavelengths between 200 and 850 nm. The spectrometer and detection probe were purchased from Stellar Net Inc. To measure plasma radius in DI water, a transparent glass plate was used to replace part of the container, as illustrated in FIG. 1. The optical probe was placed 3.5 cm in front of the plasma jet nozzle. Integration time for collecting data was set to 100 ms.

Figure 3:
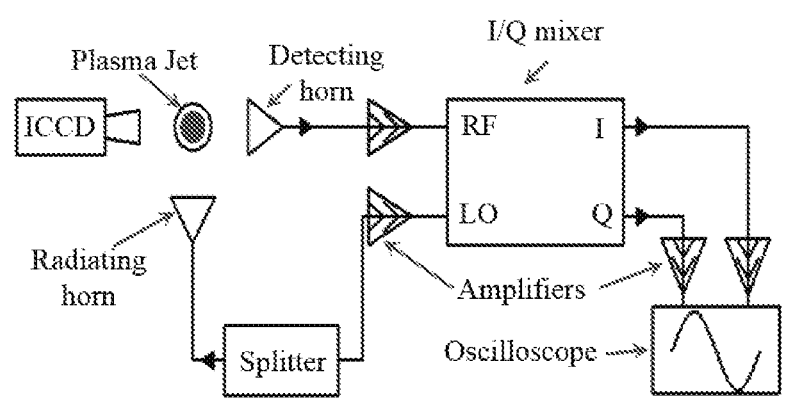
FIG. 3 is an illustration of a Rayleigh microwave scattering (RMS) system for the measurement of the density of discharged plasmas, in accordance with various embodiments of the present disclosure.

Rayleigh microwave scattering (RMS). Plasma density was measured using an RMS system as schematically illustrated in FIG. 3. As illustrated, the RMS system includes a detecting horn and a radiating horn for detection and radiation of microwaves signals, respectively. The scattered signal was measured after the linearly polarized microwave radiation was scattered on the collinearly oriented plasma channel. A homodyne I/Q Mixer providing in-phase (I) and quadrature (Q) outputs was used to detect the scattered signal. For the entire range of scattered signals, the amplifiers and mixer were operated in linear mode. Plasma density was obtained from plasma conductivity by using the following expression:

$$\sigma = \frac{2.82 \times 10^{-4} n_e v_m}{(w^2 + v_m^2)}$$

where $v_m$ is the frequency of the electron-neutral collisions, $n_e$ is the plasma density, and w is the angular frequency. Plasma conductivity can be expressed as U=AσV, where A=263.8 VΩ/cm² and U is sqrt($I^2+Q^2$). The volume of the plasma column was determined from the intensified charged-coupled device (ICCD) images. The radius (R) of the streamer column was determined from the size of the central highly luminous filament.

In situ measurement of ROS and RNS. For comparative study of $N_2$, He, and Ar, ROS and RNS levels in solution were analyzed after 30 min of plasma produced in 200 ml DI water. RNS was measured using the Griess Reagent System (Promega Corporation). All detection steps were performed according to the manufacturer's instructions. Absorbance was measured at 540 nm by a Synergy H1 Hybrid Multi-Mode Microplate Reader.

A Fluorimetric Hydrogen Peroxide Assay Kit (Sigma-Aldrich) was used for $H_2O_2$ measurement. For $H_2O_2$ measurement, we added 50 μl of standard curve samples, controls, and experimental samples were added to 96-well flat-bottom black plates, and then 50 μl of Master Mix was added to each well. The plates were incubated for 20 min at room temperature in dark conditions and detected fluorescence using the Synergy H1 Hybrid Multi-Mode Microplate Reader at Ex/Em: 540/590 nm.

Hydroxyl free radical levels were measured by utilizing a methylene blue solution. A 0.01 g/L of methylene blue (MB) in DI water was treated with plasma for 0, 5, 10, 20, and 30 min. A total of 100 μL/well of these solutions were added in triplicate to a black 96-well clear bottom plate. The absorbance was measured at 664 nm with a microplate reader.

Cell viability assays. MTT (3-(4, 5-dimethylthiazol-2-yl)-2,5-diphenyltetrazolium bromide) assay (from Sigma-Aldrich®) was used to monitor cell viability. The cells were plated in 96-well flat-bottomed microplates at a density of 3000 cells in 100 μl of compete culture medium per well. Cells were then incubated for one day to ensure proper cell adherence and stability. Confluence of each well was ensured to be at ~40%. Then 30 μl of DMEM, DI water, and plasma solutions were placed into the wells to evaluate their effects on the cells. After additional incubation at 37° C. for 24 and 48 h, the original culture medium was aspirated, and 100 μl of MTT solution per well (5 mg thiazolyl blue tetrazolium blue in 10 ml medium) was added to each well. After another 3 h, the medium was replaced by 100 μl of MTT solvent (0.4 v/v % HCl in anhydrous isopropanol) to dissolve formazan crystals. Then, solution absorbance was determined using the Synergy H1 Hybrid Multi-Mode Microplate Reader at 570 nm.

The relative metabolic activity of the gastric cancer cells was measured with a Cell Counting Kit 8 assay (Dojindo Molecular Technologies, MD). After each incubation time point (24 and 48 h), the original culture medium was aspirated and replaced with 10 μL/well of CCK 8 reagent. The plates were incubated for 3 h at 37° C. The absorbance was measured at 450 nm using a microplate reader.

Production of CAP-Containing Solutions and Cell Viability Studies

Figure 4:
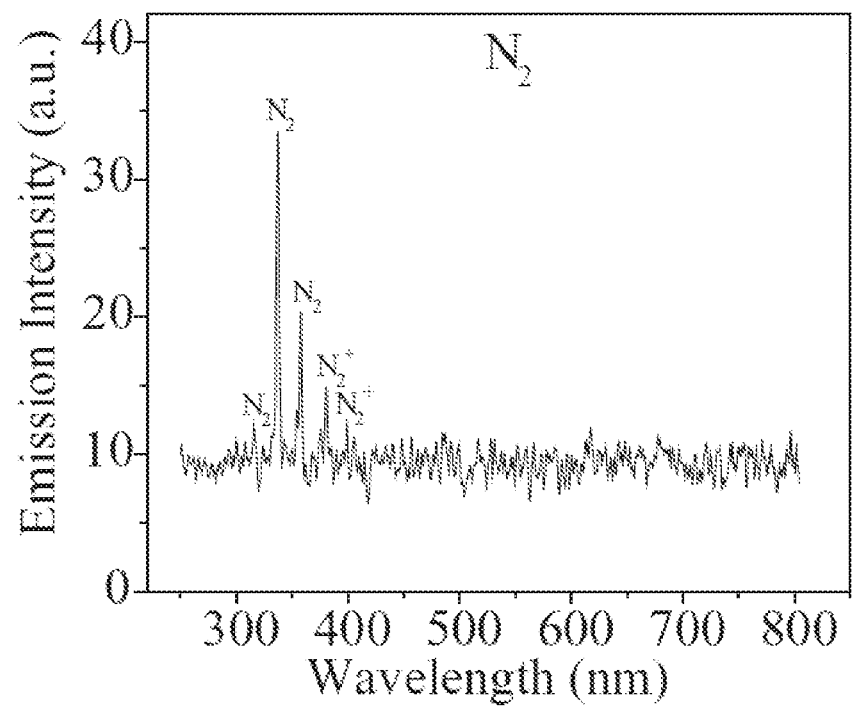
FIG. 4 is an optical emission spectrum of plasma generated in DI water from $N_2$ gas, using a system according FIG. 1, in accordance with various embodiments of the present disclosure.
Figure 5:
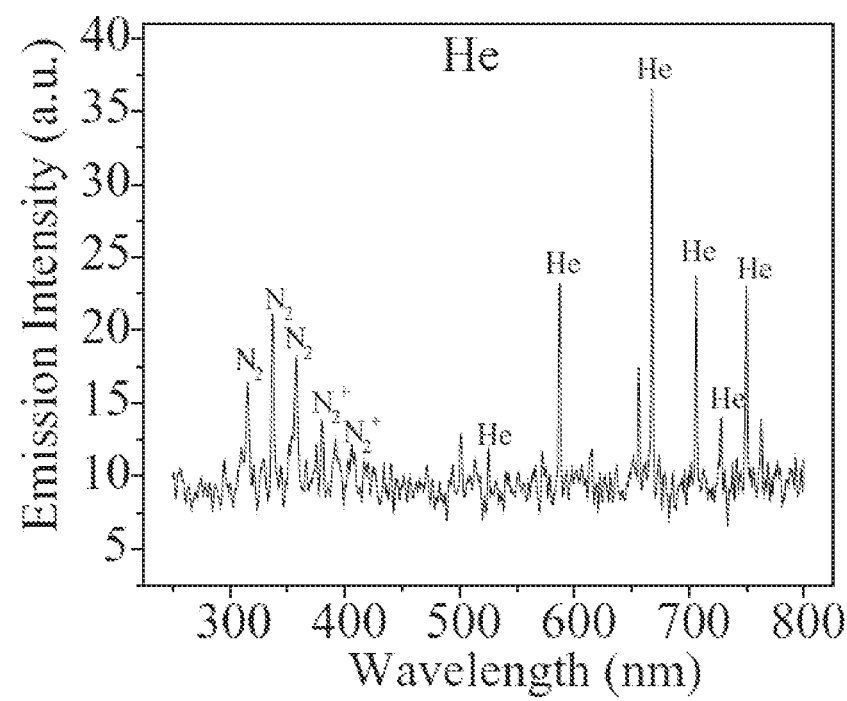
FIG. 5 is a optical emission spectrum of plasma generated in DI water from He gas, using a system according FIG. 1, in accordance with various embodiments of the present disclosure.
Figure 6:
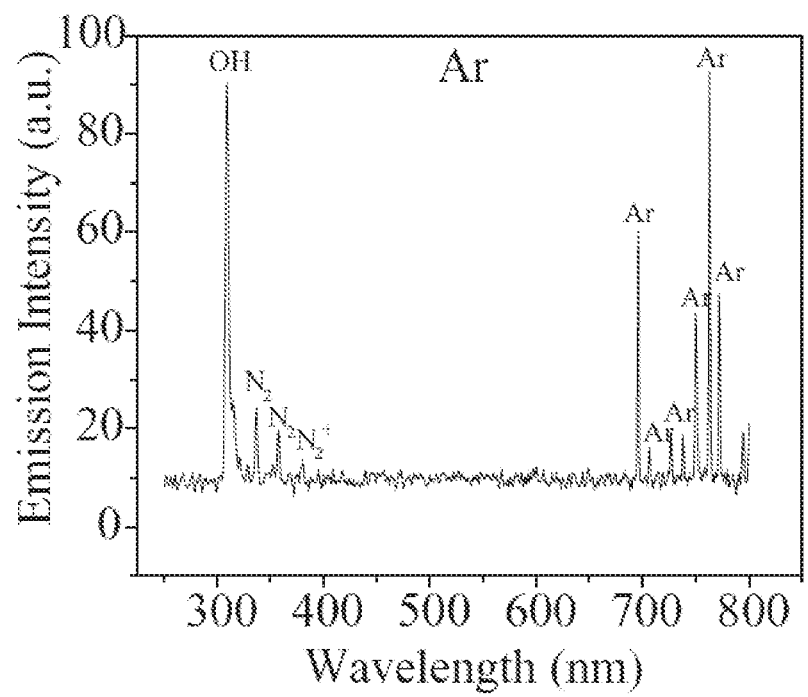
FIG. 6 is a optical emission spectrum of plasma generated in DI water from Ar gas, using a system according FIG. 1, in accordance with various embodiments of the present disclosure.

Optical characteristics of CAP-containing solution. FIGS. 4-6 are optical emission spectra of plasma generated in DI water from $N_2$, He, and Ar carrier gases, respectively, using a system according FIG. 1. Using $N_2$ as a carrier gas leads to the formation of a $N_2$ second-positive system ($C^3\Pi_u$-$B^3\Pi_g$) with peaks at 316, 337, and 358 nm. There were very weak ·NO emission lines in the range of 250-300 nm. When Ar was used, a high-intensity ·OH peak at 309 nm was observed as shown in FIG. 6. Naturally, when Ar and He were used lines in the range of 600-800 nm were observed as shown in FIGS. 5 and 6. Overall higher emission intensity was found when Ar was the carrier gas. The ·OH peak intensity was almost the same as that of Ar in the case in Ar plasma.

Figure 7:
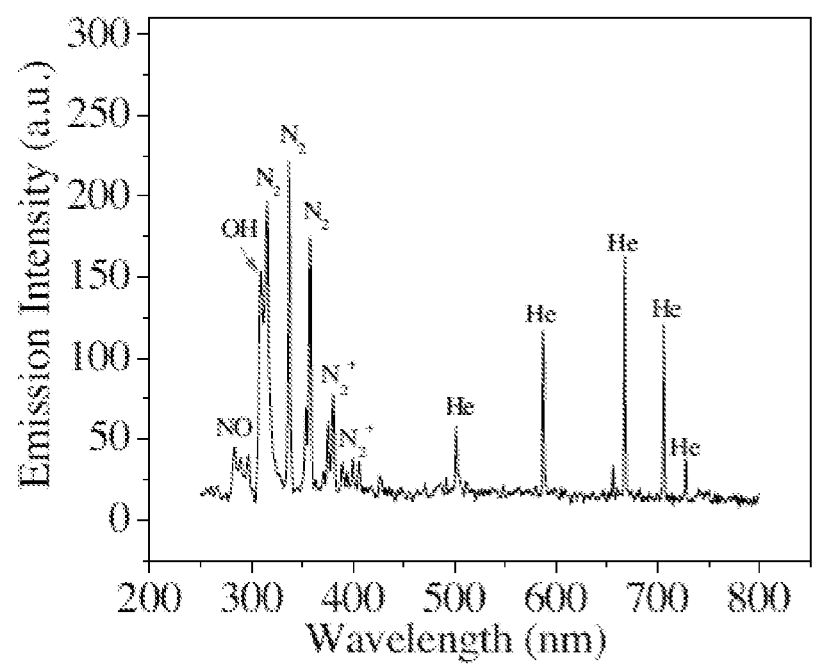
FIG. 7 is a optical emission spectrum of plasma generated in DI water from He gas, using a system according FIG. 1 with modified plasma generation parameters, in accordance with various embodiments of the present disclosure.

FIG. 7 is an optical emission spectrum of plasma generated in DI water from He carrier gas, using a system according FIG. 1, using a modified set of preparation parameters. In the modified set of preparation procedures, the peak-peak voltage was about 7 kV and the average current was about 0.40 mA, the frequency of the discharge generated in DI water was around 25 kHz, and a He flow rate of 0.4 L/min was used. As shown, more pronounced formation of ·OH and ·NO is observed as compared to FIG. 5.

Electron densities of CAP-containing solutions. FIGS. 8-10 are images of plasma generated in DI water from $N_2$, He, and Ar carrier gases using a system according FIG. 1. One can see that the plasma generated in DI water using $N_2$ is very weak, while the plasma generated in DI water using Ar has the strongest intensity.

Due to the limited access of submerged CAP (FIGS. 8-10), the electron density of plasma generated in DI water from $N_2$, He, and Ar carrier gases using a system according FIG. 2 was measured using the above described RMS system. FIGS. 11-13 are graphical representations of the electron density of plasma generated in DI water from $N_2$, He, and Ar, respectively. Each of FIGS. 11-13 also include an ICCD image of the corresponding plasma generated in DI water. As can be seen, the electron densities of $N_2$, He and Ar were about $2.3 \times 10^{11}/cm^3$, $1.4 \times 10^{12}/cm^3$, and $2.2 \times 10^{12}/cm^3$, respectively.

Figure 14:
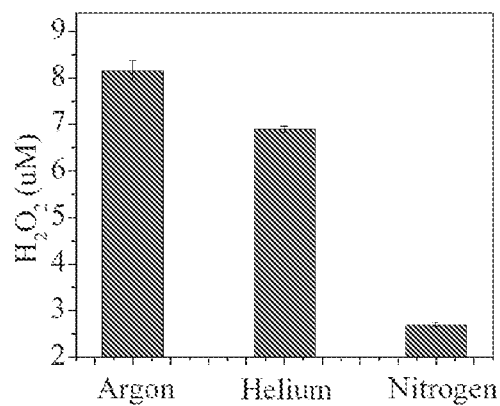
FIG. 14 is a bar chart illustrating the concentrations of $H_2O_2$ produced in CAP-containing solutions, by a system according to FIG. 1 after 30 minutes of plasma discharge, in accordance with various embodiments of the present disclosure.
Figure 15:
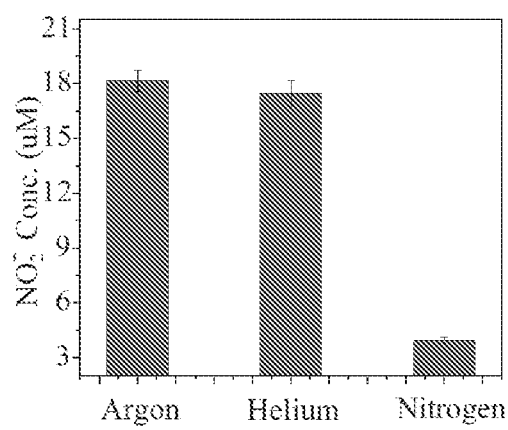
FIG. 15 is bar chart illustrating the concentrations of $NO_2^-$ produced in CAP-containing solutions, by a system according to FIG. 1 after 30 minutes of plasma discharge, in accordance with various embodiments of the present disclosure.
Figure 16:
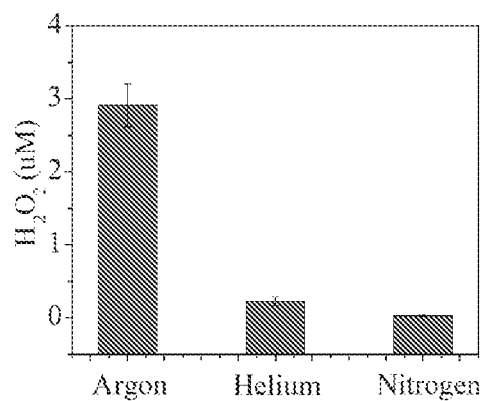
FIG. 16 is a bar chart illustrating the concentrations of $H_2O_2$ produced in CAP-containing solutions, by a system according to FIG. 2 after 30 minutes of plasma discharge, in accordance with various embodiments of the present disclosure.
Figure 17:
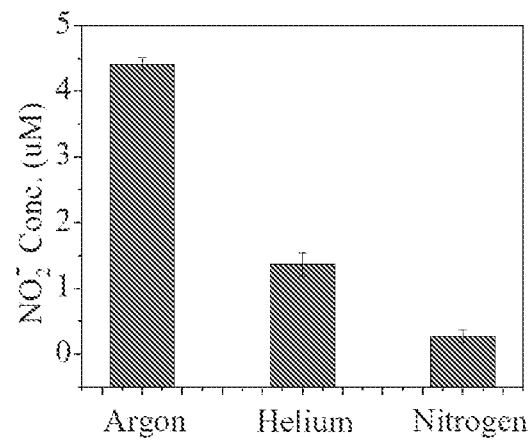
FIG. 17 is a bar chart illustrating the concentrations of $NO_2^-$ produced in CAP-containing solutions, by a system according to FIG. 2 after 30 minutes of plasma discharge, in accordance with various embodiments of the present disclosure.

ROS and RNS concentrations of CAP-containing solutions and effect of CAP-solutions on MDA-MB-231 breast cancer cell viability; comparison between $N_2$, He, and Ar carrier gases. Plasma discharged in water produces reactive species such as superoxide, the hydroxyl radical, singlet oxygen, and nitric oxide. These relatively short-lived reactive species may be converted to relatively long-lived species such as hydrogen peroxide ($H_2O_2$), nitrite ($NO_x$), and other uncertain species. $H_2O_2$ and $NO_x$ are known to induce cell proliferation as well as cell death. $H_2O_2$ is known to induce both apoptosis and necrosis, while $NO_x$ can induce cell death via DNA double-strand breaks. On the other hand, previous studies have indicated that $NO_2^-$ acts in synergy with $H_2O_2$ to enhance cell death in normal and tumor cell lines. Therefore, the effect of $H_2O_2$ and $NO_x$ generated by plasma discharged in water on breast cancer cells is investigated herein. To compare ROS and RNS production efficiency in a submerged CAP system (as illustrated in FIG. 1) and a CAP system jetting plasma outside the DI water (as illustrated in FIG. 2), the concentration of $H_2O_2$ and $NO_2^-$ were measured. FIGS. 14 and 15 are bar charts illustrating the concentrations of $H_2O_2$ and $NO_2^-$ produced by a submerged CAP system according to FIG. 1 after 30 minutes of plasma discharge. FIGS. 16 and 17 are bar charts illustrating the concentrations of $H_2O_2$ and $NO_2^-$ produced by the CAP system jetting plasma outside the DI water according to FIG. 2 after 30 minutes of plasma discharge. In these examples, CAP is formed in 200 mL of DI water. As can be observed, the $H_2O_2$ and $NO_2^-$ concentrations are highest in the case of Ar as a carrier gas, and lowest when $N_2$ is used as a carrier gas. While Ar produced the highest concentrations of $H_2O_2$ and $NO_2^-$ in CAP-containing solutions in both systems, the use of the submerged CAP system showed far greater increases in $H_2O_2$ and $NO_2^-$ concentrations for the CAP-containing solutions formed from helium and nitrogen relative to the use of a CAP system jetting plasma outside the DI water. When argon was used as the carrier gas, CAP-containing solutions made using a submerged CAP system produced solutions having an $H_2O_2$ concentration about 280% higher and a $NO_2^-$ concentration about 410% higher than the same formed using a CAP system jetting plasma outside the DI water. When helium was used as the carrier gas, CAP-containing solutions made using a submerged CAP system produced solutions having an $H_2O_2$ concentration about 2,270% higher and a $NO_2^-$ concentration about 1,260% higher than the same formed using a CAP system jetting plasma outside the DI water. When nitrogen was used as the carrier gas, CAP-containing solutions made using a submerged CAP system produced solutions having an $H_2O_2$ concentration about 2,700% higher and a $NO_2^-$ concentration about 1,000% higher than the same formed using a CAP system jetting plasma outside the DI water.

Figure 18:
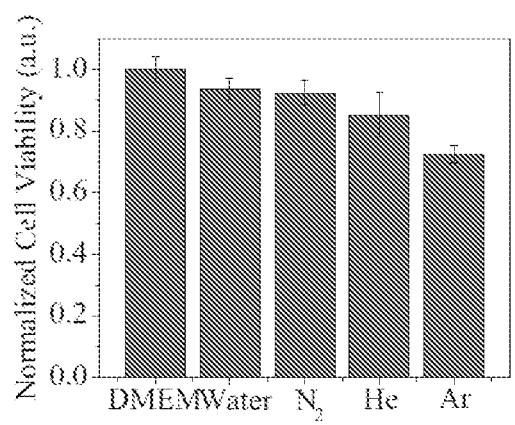
FIG. 18 is a bar chart illustrating the cell viability of MDA-MB-231 cancer cells exposed to DMEM, DI water, CAP-containing solutions formed using a system according to FIG. 1 and $N_2$ gas, He gas, and Ar gas for a period of 24 hours, in accordance with various embodiments of the present disclosure.
Figure 19:
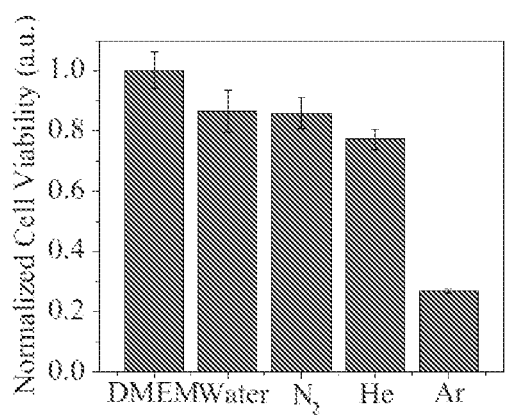
FIG. 19 is a bar chart illustrating the cell viability of MDA-MB-231 cancer cells exposed to DMEM, DI water, CAP-containing solutions formed using a system according to FIG. 1 and $N_2$ gas, He gas, and Ar gas for a period of 48 hours, in accordance with various embodiments of the present disclosure.
Figure 20:
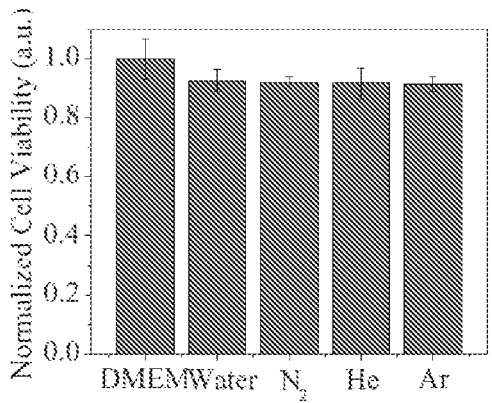
FIG. 20 is a bar chart illustrating the cell viability of MDA-MB-231 cancer cells exposed to DMEM, DI water, CAP-containing solutions formed using a system according to FIG. 2 and $N_2$ gas, He gas, and Ar gas for a period of 24 hours, in accordance with various embodiments of the present disclosure.
Figure 21:
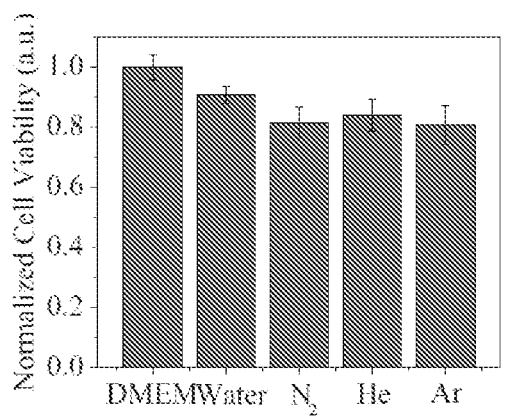
FIG. 21 is a bar chart illustrating the cell viability of MDA-MB-231 cancer cells exposed to DMEM, DI water, CAP-containing solutions formed using a system according to FIG. 2 and $N_2$ gas, He gas, and Ar gas for a period of 48 hours, in accordance with various embodiments of the present disclosure.

The above CAP-containing solutions were applied to MDA-MB-231 cancer cells. DMEM and untreated DI water were used as controls. FIG. 18 is a bar chart illustrating the cell viability of the cancer cells exposed to DMEM, DI water, a CAP-containing solution formed using $N_2$ as the carrier gas, a CAP-containing solution formed using He as the carrier gas, and a CAP-containing solution formed using Ar as the carrier gas for a period of 24 hours. FIG. 19 is a bar chart illustrating the cell viability of the cancer cells exposed to DMEM, DI water, a CAP-containing solution formed using $N_2$ as the carrier gas, a CAP-containing solution formed using He as the carrier gas, and a CAP-containing solution formed using Ar as the carrier gas for a period of 48 hours. In FIGS. 18 and 19, the CAP-containing-solutions were produced by a system according to FIG. 1. FIG. 20 is a bar chart illustrating the cell viability of the cancer cells exposed to DMEM, DI water, a CAP-containing solution formed using $N_2$ as the carrier gas, a CAP-containing solution formed using He as the carrier gas, and a CAP-containing solution formed using Ar as the carrier gas for a period of 24 hours. FIG. 21 is a bar chart illustrating the cell viability of the cancer cells exposed to DMEM, DI water, a CAP-containing solution formed using $N_2$ as the carrier gas, a CAP-containing solution formed using He as the carrier gas, and a CAP-containing solution formed using Ar as the carrier gas for a period of 48 hours. In FIGS. 20 and 21, the CAP-containing solutions were produced by a system according to FIG. 2.

When incubated for 24 h, cell viability decreased by approximately 27.4% and 14.7% when treated with Ar CAP-containing solution and He CAP-containing solution, respectively, when compared with DMEM solution (FIG. 18). Only a slight decrease in cell viability was observed in the case of DI water and $N_2$ plasma solution. For the 48 h treatment, viability decreased by approximately 73.1%, 22.8%, 14.1%, and 13.5% when cells were treated with Ar CAP-containing solution, He CAP-containing solution, $N_2$ CAP-containing solution, and DI water, respectively (FIG. 19). Thus, the strongest effect can be observed in the case of the Ar CAP-containing solution, while smallest effect was observed in the case of the $N_2$ plasma CAP-containing solution. Comparing cell treatment results stimulated by the submerged CAP system (FIGS. 18 and 19) and the CAP system jetting plasma outside the DI water (FIGS. 20 and 21), it can be concluded that the strongest effect is shown in the Ar CAP-containing solution generated in DI water.

Figure 22:
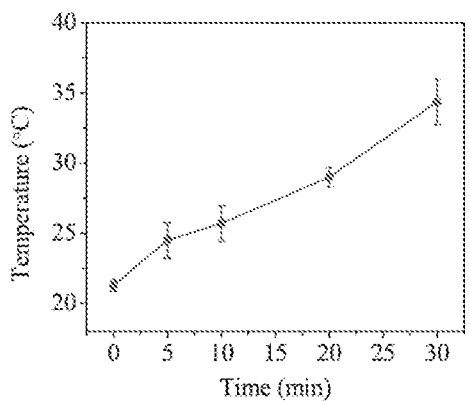
FIG. 22 is a graphical display illustrating temperature changes of CAP-containing solutions formed by different Ar plasma discharge durations, in accordance with various embodiments of the present disclosure.
Figure 23:
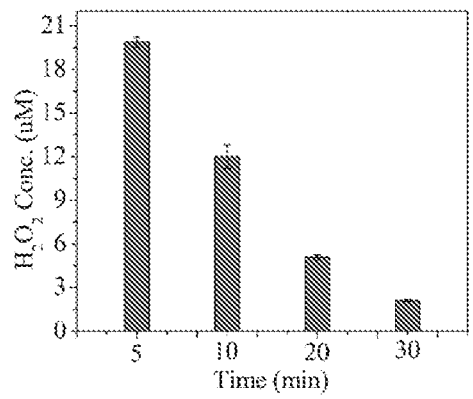
FIG. 23 is bar chart illustrating changes in the concentration of $H_2O_2$ in the CAP-containing solutions of FIG. 22 over time, in accordance with various embodiments of the present disclosure.
Figure 24:
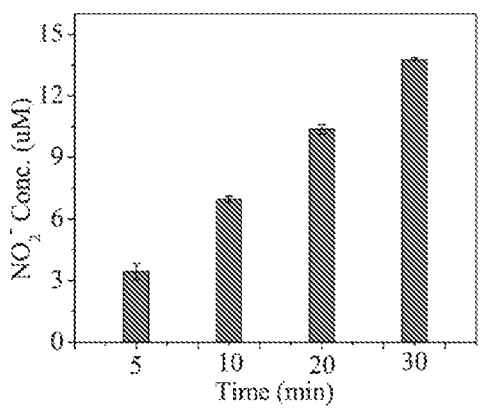
FIG. 24 is bar chart illustrating changes in the concentration of $NO_2^-$ in the CAP-containing solutions of FIG. 22 over time, in accordance with various embodiments of the present disclosure.

ROS and RNS concentrations of CAP-containing solutions and effect of CAP-solutions on NCI-N87 gastric cancer cell viability; Ar as carrier gas. In this example, CAP-containing solutions were formed using a system according FIG. 1, with Ar as the carrier gas, in DI water. The submerged average discharge current was 0.23 mA and the peak voltage was about 8 kV. The frequency of the discharge generated in DI water is around 6.25 kHz. The temperature change of the plasma solutions for different Ar plasma discharge durations is illustrated in FIG. 22. The highest temperature increase to 34.4±1.6° C. is achieved at 30 min plasma discharge duration. FIG. 23 is a bar chart showing changes in the concentration of $H_2O_2$ in the CAP-containing solutions over time. As can be seen the concentration of $H_2O_2$ decreases over time. According to the Arrhenius theory, the decomposition rate of $H_2O_2$ increases with the temperature. As shown in FIG. 22, above, the temperature of the CAP-containing solution increases with the treatment time. Without being bound to any particular theory, the increase in temperature may explain the decrease of $H_2O_2$ concentration. FIG. 24 is a bar chart showing the concentration of $NO_2^-$ in the CAP-containing solutions over time. Without being bound to any particular theory, the production of $NO_2^-$ is believed to be due to the presence of $N_2$ from either air surrounding the DI water or from the industrial grade argon itself.

Figure 25:
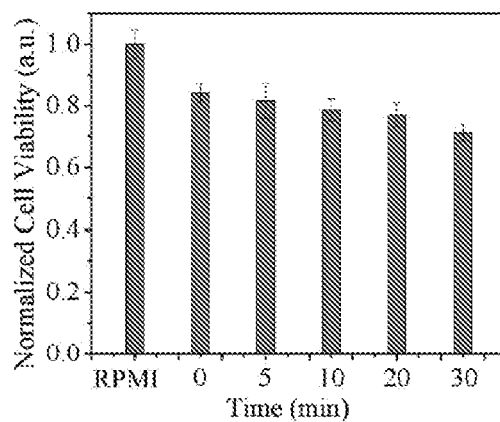
FIG. 25 is a bar chart illustrating the viability of NCI-N87 human gastric cancer cells exposed to RPMI, DI water (time=0 min), and CAP-containing solutions (made by 5, 10, 20, and 30 minute durations of Ar plasma discharge, respectively) for 24 hours, in accordance with various embodiments of the present disclosure.

The CAP-containing solutions produced above were applied to NCI-N87 gastric cancer cells. RPMI and untreated DI water were used as the controls. FIG. 25 is a bar chart illustrating the viability of the human gastric cancer cells exposed to RPMI, DI water (time=0 min), and CAP-containing solutions (made by 5, 10, 20, and 30 minute durations of Ar plasma discharge, respectively) for 24 hours. At 24 h, the viability decreased by 15.8% when the cells were treated with DI water in comparison with the RPMI control condition. The viability of cells treated with the CAP-containing solutions were lower than the viability of the cells treated with the DI water.

Figure 26:
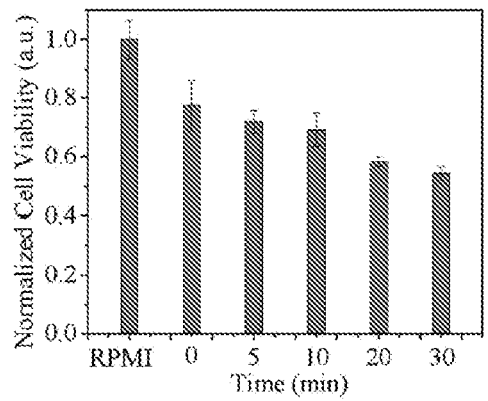
FIG. 26 is a bar chart illustrating the viability of NCI-N87 human gastric cancer cells exposed to RPMI, DI water (time=0 min), and CAP-containing solutions (made by 5, 10, 20, and 30 minute durations of Ar plasma discharge, respectively) for 48 hours, in accordance with various embodiments of the present disclosure.

FIG. 26 is a bar chart illustrating the viability of the human gastric cancer cells exposed to RPMI, DI water (time=0 min), and CAP-containing solutions (made by 5, 10, 20, and 30 minute durations of Ar plasma discharge, respectively) for 48 hours. At 48 h, the viability of the cell decreased by approximately 22.6%, 28.2%, 30.9%, 41.6%, and 45.7%, respectively, according to treatment duration. A decrease in cell viability was accompanied with an increase in the concentration of $NO_2^-$ and a decrease in the concentration of $H_2O_2$. Over both treatment intervals (i.e., 24 h and 48 h), the strongest effect can be observed at 30 min plasma solution.

ROS and RNS are important signal mediators that regulate cell death. When the cell is stimulated by the environmental stress or other factors, it produces ROS that are potential signaling molecules. An extreme amount of ROS in the cells may cause DNA damage, genetic instability, cellular injury, and eventually induce apoptosis. RNS are pleiotropic mediators and signaling molecules involved in a large number of cell functions. In some situations, RNS activate the transduction pathways causing cells apoptosis and are capable of inducing cell death via DNA double-strands break/apoptosis. On the other hand, ROS reacts with RNS to form peroxynitrite. This leads either to caspase activation followed by apoptosis or to lipid peroxidation, protein nitration, or oxidation, which can result in necrosis. The results in FIGS. 23 and 24 show that the ROS concentration is highest at the 5 minute Ar plasma discharge duration while the RNS concentration is highest at the 30 minute Ar plasma discharge duration. The trend of cell death can be attributed to the increase in RNS concentration with increasing treatment time. A synergistic effect of RNS and ROS is suspected to play a key role in the apoptosis effect of plasma solution. In fact, RNS play a more important role that ROS in the gastric cancer cell apoptosis under the above experimental conditions.

Figure 27:
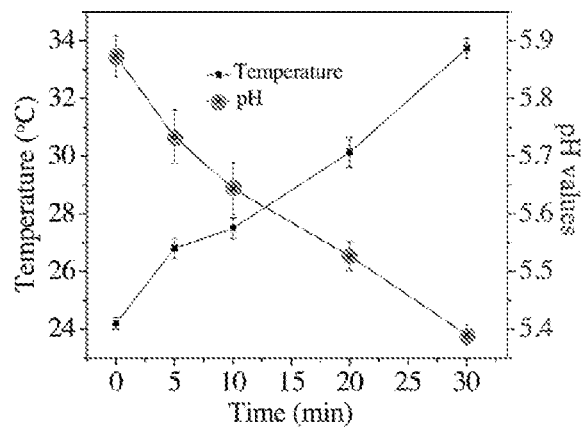
FIG. 27 is a graphical display illustrating how the temperature of CAP-containing solutions increase while pH values decrease with He plasma discharge time, in accordance with various embodiments of the present disclosure.
Figure 28:
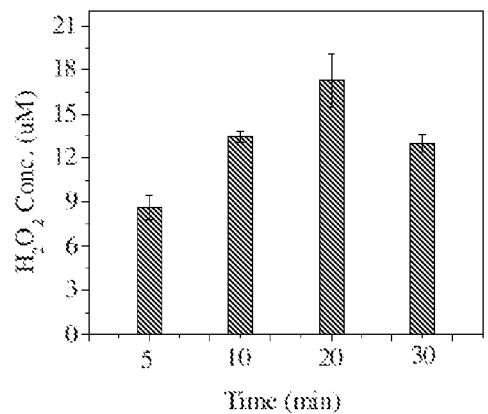
FIG. 28 is a bar chart illustrating $H_2O_2$ concentration of CAP-containing solutions after 5, 10, 20, and 30 min of He plasma discharge into DI water, in accordance with various embodiments of the present disclosure.
Figure 29:
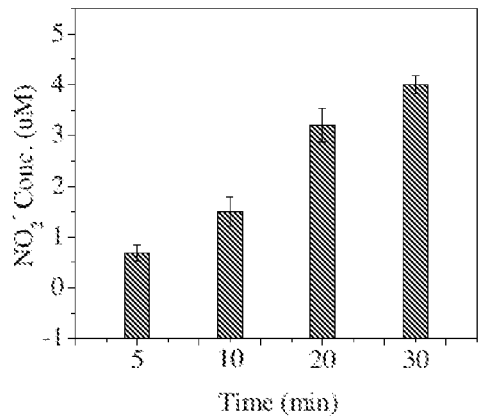
FIG. 29 is a bar chart illustrating $NO_2^-$ concentration of CAP-containing solutions after 5, 10, 20, and 30 min of He plasma discharge into DI water, in accordance with various embodiments of the present disclosure.
Figure 30:
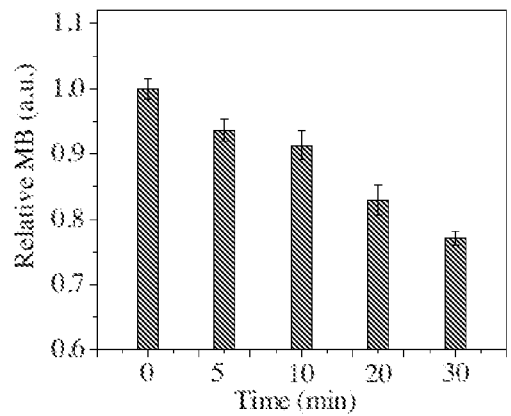
FIG. 30 is a bar chart illustrating hydroxyl radical (·OH) concentration of CAP-containing solutions, after 5, 10, 20, and 30 min of He plasma discharge into DI water, via colorimetric quantification using methylene blue, in accordance with various embodiments of the present disclosure.

ROS and RNS concentrations of CAP-containing solutions and effect of CAP-solutions on cancer cell viability; He as carrier gas. In this example, CAP-containing solutions were formed using a system according FIG. 1, with He as the carrier gas, in DI water. The peak-peak voltage was about 7 kV and the average current was about 0.40 mA. The frequency of the He plasma discharge generated in DI water was around 25 kHz. Industrial grade helium with a flow rate of 0.4 L/min was used for testing. The plasma produced inside DI water generated four CAP-containing solutions after 5, 10, 20, and 30 min of He plasma discharge into the DI water. FIG. 27 is a graphical display illustrating how the temperature of CAP-containing solutions increase while pH values decrease with He plasma discharge time. FIG. 28 is a bar chart illustrating $H_2O_2$ concentration in the CAP-containing solutions after 5, 10, 20, and 30 min of He plasma discharge into the DI water. As shown, the concentration of $H_2O_2$ increased with He plasma discharge time up to 20 minutes. Between 20 and 30 minutes, however, the $H_2O_2$ concentration decreased. FIG. 29 is a bar chart illustrating $NO_2^-$ concentration in the CAP-containing solutions after 5, 10, 20, and 30 min of He plasma discharge into the DI water. Without being bound to any particular theory, the production of $NO_2^-$ is believed to be due to the presence of $N_2$ from either air surrounding the DI water or from the industrial grade helium itself. FIG. 30 is a bar chart illustrating hydroxyl radical (·OH) concentration in the CAP-containing solutions, after 5, 10, 20, and 30 min of He plasma discharge into the DI water, via colorimetric quantification using methylene blue.

Figure 31:
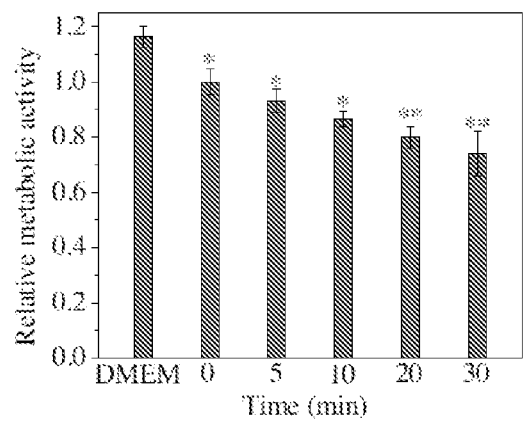
FIG. 31 is a bar chart illustrating the relative metabolic activity of MDA-MB-231 breast cancer cells when exposed to DMEM, DI water (time=0 minutes), and CAP-containing solutions (made by 5, 10, 20, and 30 minute durations of He plasma discharge, respectively) for 24 hours, in accordance with various embodiments of the present disclosure.
Figure 32:
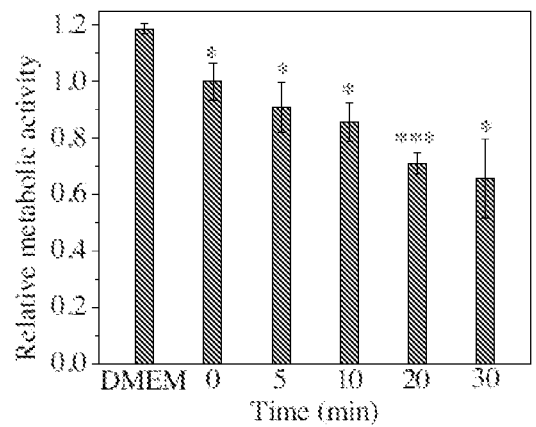
FIG. 32 is a bar chart illustrating the relative metabolic activity of MDA-MB-231 breast cancer cells when exposed to DMEM, DI water (time=0 minutes), and CAP-containing solutions (made by 5, 10, 20, and 30 minute durations of He plasma discharge, respectively) for 48 hours, in accordance with various embodiments of the present disclosure.
Figure 33:
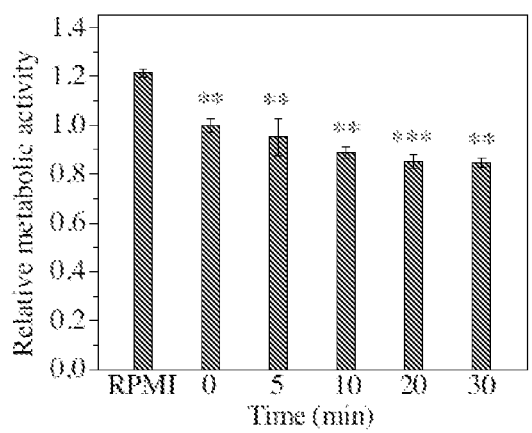
FIG. 33 is a bar chart illustrating the relative metabolic activity of NCI-N87 gastric cancer cells when exposed to RPMI, DI water (time=0 minutes), and CAP-containing solutions (made by 5, 10, 20, and 30 minute durations of He plasma discharge, respectively) for 24 hours, in accordance with various embodiments of the present disclosure.
Figure 34:
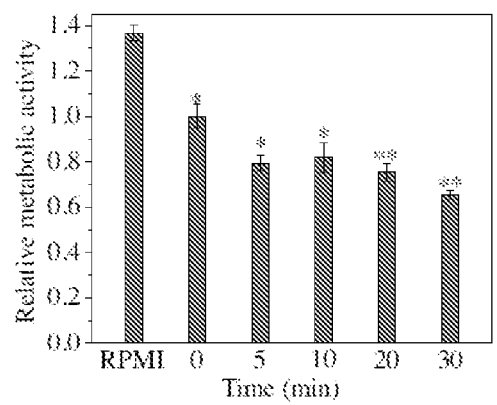
FIG. 34 is a bar chart illustrating the relative metabolic activity of NCI-N87 gastric cancer cells when exposed to RPMI, DI water (time=0 minutes), and CAP-containing solutions (made by 5, 10, 20, and 30 minute durations of He plasma discharge, respectively) for 48 hours, in accordance with various embodiments of the present disclosure.

FIG. 31 is a bar chart illustrating the relative metabolic activity of MDA-MB-231 breast cancer cells when exposed to DMEM, DI water (time=0 minutes), and CAP-containing solutions (made by 5, 10, 20, and 30 minute durations of He plasma discharge, respectively) for 24 hours. FIG. 32 is bar chart illustrating the relative metabolic activity of MDA-MB-231 breast cancer cells when exposed to DMEM, DI water (time=0 minutes), and CAP-containing solutions (made by 5, 10, 20, and 30 minute durations of He plasma discharge, respectively) for 48 hours. FIG. 33 is a bar chart illustrating the relative metabolic activity of NCI-N87 gastric cancer cells when exposed to RPMI, DI water (time=0 minutes), and CAP-containing solutions (made by 5, 10, 20, and 30 minute durations of He plasma discharge, respectively) for 24 hours. FIG. 34 is bar chart illustrating the relative metabolic activity of NCI-N87 gastric cancer cells when exposed to RPMI, DI water (time=0 minutes), and CAP-containing solutions (made by 5, 10, 20, and 30 minute durations of He plasma discharge, respectively) for 48 hours. In FIGS. 31-34, a student t-test was performed, and the statistical significance compared to cells present in DMEM/RPMI (first bar) is indicated as *$p<0.05$, $p<0.01$, *$p<0.005$. (n=3).

FIGS. 31 and 33 show that, after 24 h, the relative metabolic activity of the breast and gastric cancer cells treated with DI water (0 min) decreased to 14.0 and 17.6% in comparison to the DMEM/RPMI control condition. The relative metabolic activity of the breast and gastric cancer cells treated by CAP-containing solution was lower than that of the untreated DI water (0 min) and dropped with increasing He plasma discharge time. After 48 h of incubation, the cell relative metabolic activity of the breast cancer cells (compared with DMEM) decreased by approximately 23.4, 27.8, 40.1, and 44.7%, respectively, according to CAP-containing solutions formed by 5, 10, 20, and 30 minute He plasma discharge durations (FIG. 32). After 48 h of incubation, the cell relative metabolic activity of the gastric cancer cells (compared with RPMI) decreased by 42.0, 40.3, 45.0, and 52.1%, respectively, according to CAP-containing solutions formed by He plasma discharge durations ranging from 5 to 30 min. (FIG. 34). The most significant effect based on the relative metabolic activity was observed for the 30 min plasma treated solution.

A decrease in cell relative metabolic activity was accompanied with an increase in the concentration of $NO_2^-$ and $H_2O_2$. ROS and RNS are known to induce cell proliferation as well as cell death. ROS are known to induce both apoptosis and necrosis, while RNS can induce cell death via damage DNA. The results show that the ROS concentration is highest after 20 minutes of plasma discharge while the RNS concentration is highest after 30 minutes of plasma discharge. The trend of cell death can be attributed to the increase of RNS concentration with treatment time. A synergistic effect of RNS and ROS is suspected to play a key role in the apoptosis of the plasma solutions. $NO_2^-$ concentration increased with He plasma discharge time, while $H_2O_2$ concentration decreased after 20 min of He plasma discharge. Thus, it is possible that no $H_2O_2$ is present in solutions treated for longer than 30 minutes.

Statements of the Disclosure include:

Statement 1: A composition of matter, the composition of matter comprising a solvent, and a cold atmospheric plasma dissolved in the solvent to form a solution.

Statement 2: A composition of matter according to Statement 1, wherein the solvent comprises deionized (DI) water, a water-based electrolyte solution, a phosphate-buffered saline (PBS) solution, a glucose solution, a cell culture medium, or any combination thereof.

Statement 3: A composition of matter according to Statement 1 or Statement 2, wherein the solution comprises one or more of reactive oxygen species and reactive nitrogen species.

Statement 4: A composition of matter according to Statement 3, wherein the reactive oxygen species comprise one or more of hydroxyl radicals ($\cdot OH$), hydrogen peroxide ($H_2O_2$), singlet oxygen ($^1O_2$), and superoxide radicals ($\cdot O_2^-$).

Statement 5: A composition of matter according to Statement 3 or Statement 4, wherein the reactive nitrogen species comprise one or more of nitric oxide ($\cdot NO$), nitrogen cation ($N_2^+$), nitrite ion ($NO_2^-$), and peroxynitrite ion ($ONOO^-$).

Statement 6: A composition of matter according to any one of Statements 1-5, wherein the solution has a hydrogen peroxide ($H_2O_2$) concentration ranging from about 0.5 µM to about 25 µM.

Statement 7: A composition of matter according to any one of Statements 1-6, wherein the solution has a nitrite ion ($NO_2^-$) concentration ranging from about 0.5 µM to about 25 µM.

Statement 8: A method of making a cold atmospheric plasma (CAP)-containing solution, the method comprising ionizing a gas in a plasma formation chamber to form a cold atmospheric plasma (CAP), discharging a jet or stream of the CAP from the plasma formation chamber, and dissolving the jet or stream of the CAP into a solvent to form a CAP-containing solution.

Statement 9: A method according to Statement 8, further comprising storing the CAP-containing solution at a temperature ranging from about 25° C. to about −40° C.

Statement 10: A method according to Statement 8, further comprising storing the CAP-containing solution at a temperature ranging from about 2° C. to about −25° C.

Statement 11: A method according to any one of Statements 8-10, further comprising storing the CAP-containing solution in a dark location.

Statement 12: A method according to any one of Statements 8-11, wherein ionization of the gas is conducted by application of a voltage ranging from about 1 kV to about 15 kV.

Statement 13: A method according to any one of Statements 8-11, wherein ionization of the gas is conducted by application of a voltage ranging from about 2 kV to about 5 kV.

Statement 14: A method according to Statement 12 or Statement 13, wherein the applied voltage has frequency ranging from about 5 kHz to about 45 kHz.

Statement 15: A method according to Statement 12 or Statement 13, wherein the applied voltage has frequency ranging from about 30 kHz to about 35 kHz.

Statement 16: A method according to any one of Statements 8-15, wherein the plasma formation chamber is at least partially submerged in the solvent such that the jet or stream of the CAP is discharged directly in the solvent.

Statement 17: A method according to any one of Statements 8-16, wherein the gas comprises nitrogen ($N_2$), helium (He), argon (Ar), or any combination thereof.

Statement 18: A method according to any one of Statements 8-17, wherein formation of the CAP and the discharge of the jet or stream of the CAP is performed over a period of time ranging from 30 seconds to about 1 hour.

Statement 19: A method according to any one of Statements 8-17, wherein formation of the CAP and the discharge of the jet or stream of the CAP is performed over a period of time ranging from 5 minutes to about 30 minutes.

Statement 20: A method according to any one of Statements 8-19, further comprising delivering the gas to the plasma formation chamber from a gas source.

Statement 21: A method according to Statement 20, wherein the gas is delivered to the plasma formation chamber at a rate ranging from about 0.5 L/min to about 20 L/min.

Statement 22: A method according to Statement 20, wherein the gas is delivered to the plasma formation chamber at a rate ranging from about 3 L/min to about 4 L/min.

Statement 23: A method of treating a tissue, the method comprising subjecting the tissue to a solution, the solution comprising a solvent and a cold atmospheric plasma dissolved in the solvent.

Statement 24: A method according to Statement 23, wherein the solvent comprises deionized (DI) water, a water-based electrolyte solution, a phosphate-buffered saline (PBS) solution, a glucose solution, a cell culture medium, or any combination thereof.

Statement 25: A method according to Statement 23 or Statement 24, wherein the solution comprises one or more of reactive oxygen species and reactive nitrogen species.

Statement 26: A method according to Statement 25, wherein the reactive oxygen species comprise one or more of hydroxyl radicals ($\cdot OH$), hydrogen peroxide ($H_2O_2$), singlet oxygen ($^1O_2$), and superoxide radicals ($\cdot O_2^-$).

Statement 27: A method according to Statement 25 or Statement 26, wherein the reactive nitrogen species comprise one or more of nitric oxide ($\cdot NO$), nitrogen cation ($N_2^+$), nitrite ion ($NO_2^-$), and peroxynitrite ion ($ONOO^-$).

Statement 28: A method according to any one of Statements 23-27, wherein the solution has a hydrogen peroxide ($H_2O_2$) concentration ranging from about 0.5 µM to about 25 µM.

Statement 29: A method according to any one of Statements 23-28, wherein the solution has a nitrite ion ($NO_2^-$) concentration ranging from about 0.5 µM to about 25 µM.

Statement 30: A method according to any one of Statements 23-29, wherein the tissue is an external tissue and subjecting the tissue to the solution comprises directly applying the solution to the external tissue.

Statement 31: A method according to Statement 30, wherein the solution is directly applied to the external tissue as a mist or spray.

Statement 32: A method according to any one of Statements 23-29, wherein the tissue is an internal organ, tissue or cavity and the solution is delivered to the tissue using any one of a syringe, a needle-free injector, a catheter, a cannula, a stent, and a feeding tube.

Statement 33: A method according to any one of Statements 23-29, wherein the tissue is subjected to the solution by oral administration of the solution.

Statement 34: A method according to any one of Statements 23-33, wherein the solution is formed by a method according to any one of Statements 8-22.

Statement 35: A medical dressing, the medical dressing comprising an absorbent material and a solution absorbed in the absorbent material; the solution comprising a solvent and a cold atmospheric plasma dissolved in the solvent.

Statement 36: A medical dressing, the medical dressing comprising an absorbent material and a solution absorbed in the absorbent material, wherein the solution is in accordance with any one of Statements 1-7.

Statement 37: A medical dressing, the medical dressing comprising an absorbent material and a solution absorbed in the absorbent material; the solution comprising a solvent, and a cold atmospheric plasma dissolved in the solvent, wherein the solution is formed by a method according to any one of Statements 8-22.

Statement 38: A system for producing a cold atmospheric plasma (CAP)-containing solution, the system comprising: a gas source; a plasma generating device, the plasma generating device comprising a hollow body fluidically coupled with the gas source and having a closed proximal end and an open distal end, the hollow body receiving a gas from the gas source, and at least one electrode in or about the hollow body and ionizing the gas to discharge a cold atmospheric plasma (CAP) from the open distal end; and a container having an inner portion for housing a fluid, wherein the open distal end of the plasma generating device is in fluid communication with the inner portion of the container.

Statement 39: A system according to Statement 38, wherein the container further comprises an opening located at a bottom portion of the container, at least a portion of the plasma generating device protrudes into the container through the opening, and the opening and the plasma generating device are sealingly engaged.

Statement 40: A system according to Statement 38, wherein the container further comprises an opening at a top portion of the container and the plasma generating device is in communication with the inner portion of the container via the opening.

Statement 41: A system according to any one Statements 38-40, wherein the gas source supplies one or more of nitrogen gas, helium gas, and argon gas to the plasma generating device.

Statement 42: A system according to any one Statements 38-41, wherein the hollow body of the plasma generating device further comprises a main body, a neck having a diameter smaller than the main body, and a portion inwardly tapering from the main body to the neck, wherein at least a portion of the main body defines the proximal end of the hollow body and the neck defines at least a portion of the open distal end of the hollow body.

Statement 43: A system according to Statement 42, wherein the gas is ionized and the CAP is formed in the inwardly tapering portion.

Statement 44: A system according to Statement 42 or Statement 43, wherein the at least one electrode extends around an outer surface of the neck.

Statement 45: A system according to any one Statements 38-44, further comprising a fluid housed in the container.

Statement 46: A system according to Statement 45, wherein the fluid comprises deionized (DI) water, a water-based electrolyte solution, a phosphate-buffered saline (PBS) solution, a glucose solution, a cell culture medium, or any combination thereof.

Statement 47: A system according to Statement 45 or Statement 46, wherein the CAP is discharged into the fluid as a jet or stream.

Statement 48: A system according to Statement 45 or Statement 46, wherein the CAP is discharged into the fluid as a bubble.

Statement 49: A system according to any one of Statements 38-48, wherein the at least one electrode comprises a first electrode extending longitudinally through at least a portion of the hollow body, and a second electrode extending around the hollow body near the distal end.

Statement 50: A system according to Statement 49, further comprising a high voltage power supply electrically coupled with the first electrode and the second electrode.

It will be apparent that various other modifications and adaptations of the embodiments or application will be apparent to the person skilled in the art after reading the foregoing disclosure without departing from the scope of the application and it is intended that all such modifications and adaptations come within the scope of the appended claims.

What is claimed is:

1. A system for producing a cold atmospheric plasma (CAP)-containing solution, the system comprising:
   a gas source;
   a plasma generating device, the plasma generating device comprising:
   a hollow body fluidically coupled with the gas source and having a closed proximal end and an open distal end, the hollow body receiving a gas from the gas source; and
   at least one electrode in or about the hollow body and configured to ionize the gas to discharge a cold atmospheric plasma (CAP) from the open distal end, the at least one electrode comprising a first electrode extending longitudinally through at least a portion of the hollow body, and a second electrode extending around the hollow body in proximity to the distal end, wherein a high voltage power supply is electrically coupled with the first electrode and the second electrode; and a container having an inner portion for housing a fluid, wherein the open distal end of the plasma generating device is configured to be submerged in the fluid such the CAP is discharged directly into the fluid.

2. The system of claim 1, wherein the container further comprises an opening located at a bottom portion of the container, at least a portion of the plasma generating device protrudes into the container through the opening, and the opening and the plasma generating device are sealingly engaged.

3. The system of claim 1, wherein the container further comprises an opening at a top portion of the container and the plasma generating device is in fluid communication with the inner portion of the container via the opening.

4. The system of claim 1, wherein the gas source supplies one or more of nitrogen gas, helium gas, and argon gas to the plasma generating device.

5. The system of claim 1, wherein the hollow body of the plasma generating device further comprises:
a main body,
a neck having a diameter smaller than the main body; and
a portion inwardly tapering from the main body to the neck,
wherein at least a portion of the main body defines the proximal end of the hollow body and the neck defines at least a portion of the open distal end of the hollow body.

6. The system of claim 5, wherein the gas is ionized and the CAP is formed in the inwardly tapering portion.

7. The system of claim 5, wherein the second electrode extends around an outer surface of the neck.

8. The system of claim 1, further comprising a fluid housed in the container.

9. The system of claim 8, wherein the fluid comprises deionized (DI) water, a water-based electrolyte solution, a phosphate-buffered saline (PBS) solution, a glucose solution, a cell culture medium, or any combination thereof.

10. The system of claim 8, wherein the CAP is discharged directly into the fluid as any one of a bubble, jet or stream.

11. The system of claim 1, wherein the gas source supplies helium gas to the plasma generating device.

* * * * *